(12) United States Patent  
Goldman et al.

(10) Patent No.: US 7,902,417 B2  
(45) Date of Patent: Mar. 8, 2011

(54) DUAL CATALYST SYSTEM FOR ALKANE METATHESIS

(75) Inventors: Alan S. Goldman, Highland Park, NJ (US); Maurice Brookhart, Carrboro, NC (US); Amy H. Roy, Laurel, MD (US); Ritu Ahuja, Highland Park, NJ (US); Zheng Huang, Chapel Hill, NC (US)

(73) Assignees: The University of North Carolina at Chapel Hill, Chapel Hill, NC (US); Rutgers, The State University of New Jersey, New Brunswick, NJ (US)

( * ) Notice: Subject to any disclaimer, the term of this patent is extended or adjusted under 35 U.S.C. 154(b) by 1076 days.

(21) Appl. No.: 11/482,324

(22) Filed: Jul. 7, 2006

(65) Prior Publication Data

US 2007/0060781 A1    Mar. 15, 2007

Related U.S. Application Data

(60) Provisional application No. 60/697,667, filed on Jul. 8, 2005.

(51) Int. Cl.  
*C07C 5/327* (2006.01)  
*C07C 6/08* (2006.01)

(52) U.S. Cl. .......................... 585/656; 585/708

(58) Field of Classification Search .................. 585/656, 585/708  
See application file for complete search history.

(56) References Cited

U.S. PATENT DOCUMENTS

| | | | |
|---|---|---|---|
| 3,445,541 A | 5/1969 | Heckelsberg et al. | |
| 3,657,109 A | 4/1972 | Beyaert | |
| 3,699,035 A | 10/1972 | Hughes et al. | |
| 3,718,576 A | 2/1973 | Hughes et al. | |
| 3,728,410 A | 4/1973 | Hughes | |
| 3,773,845 A | 11/1973 | Hughes | |
| 3,775,505 A | 11/1973 | Hughes | |
| 3,784,622 A | 1/1974 | Hughes | |
| 3,793,251 A | 2/1974 | Hughes | |
| 3,808,285 A | 4/1974 | Hughes | |
| 3,856,876 A | 12/1974 | Burnett | |
| 3,864,417 A | 2/1975 | Hughes | |
| 3,914,330 A | 10/1975 | Hughes | |
| 6,229,060 B1 | 5/2001 | Vidal et al. | |
| 6,441,263 B1 | 8/2002 | O'Rear et al. | |
| 6,566,568 B1 | 5/2003 | Chen | |
| 6,566,569 B1 * | 5/2003 | Chen et al. | 585/324 |
| 6,982,305 B2 | 1/2006 | Nagy | |
| 2002/0111521 A1 | 8/2002 | O'Rear | |
| 2004/0181104 A1 | 9/2004 | Yeh et al. | |
| 2005/0014987 A1 | 1/2005 | Basset et al. | |

OTHER PUBLICATIONS

Goldman AS et al. Catalytic alkane metathesis by tandem alkane dehydrogenation—olefin metathesis. Science (Apr. 14, 2006), vol. 312, pp. 257-261.

International Search Report and Written Opinion for PCT/US06/26808; date of mailing Feb. 22, 2007.

Burnett, Robert L. and Hughes, Thomas R., Mechanism and poisoning of the molecular redistribution reaction of alkanes with a dual-functional catalyst system, Journal of Catalysis 31, 55-64 (1973).

Wasilke J-C et al. Concurrent tandem catalysis. Chemical Reviews 2005; 105: 1001-1020.

\* cited by examiner

*Primary Examiner* — Tam M Nguyen  
(74) *Attorney, Agent, or Firm* — Myers Bigel Sibley & Sajovec, P.A.

(57) ABSTRACT

A method of converting at least one first alkane to a mixture of at least one low molecular weight alkane (optionally also including additional lower and/or higher molecular weight alkanes) and at least one high molecular weight alkane, comprising: reacting a first alkane in the presence of dual catalyst system comprising a first catalyst (i.e., a hydrogen transfer catalyst and preferably an iridium pincer complex catalyst) and a second catalyst (i.e., a metathesis catalyst) to produce a mixture of low and high molecular weight alkanes.

29 Claims, 6 Drawing Sheets

US 7,902,417 B2

DUAL CATALYST SYSTEM FOR ALKANE METATHESIS

RELATED APPLICATIONS

This application claims the benefit of U.S. Provisional Patent Application Ser. No. 60/697,667, filed Jul. 8, 2005, the disclosure of which is incorporated by reference herein in its entirety.

This invention was made with Government support under Grant No. CHE-0434568 from the National Science Foundation. The United States Government has certain rights to this invention.

FIELD OF THE INVENTION

The present invention concerns methods of converting alkanes to higher molecular weight alkanes and fuels such as diesel fuel, along with catalyst systems and apparatus useful in such methods.

BACKGROUND OF THE INVENTION

Rising demand for fuels and potentially diminishing supplies of crude oil (or at least limits in or volatility in the capacity to manufacture fuels from crude oil) have spurred increased interest in the production of fuels from alternative sources.

Coal, natural gas and biomass can be converted to synthesis gas (generally composed of hydrogen and carbon monoxide) in accordance with known techniques. Synthesis gas can, in turn, be converted to liquid hydrocarbons by the well-known technique of Fischer-Tropsch catalysis, which has been utilized for the production of fuels for many years. See, e.g., M. Dry, High quality diesel via the Fischer-Tropsch process-A review, *J. Chem. Technol. Biotechnol.* 77: 43-50 (2001). Fischer-Tropsch catalysis, however, produces a mixture of alkanes, many of which are of lower molecular weight and unsuitable for use as liquid hydrocarbon fuels such as gasoline and diesel fuels.

Some examples of dual catalyst systems are described in R. Burnett and T. Hughes, Mechanism and Poisoning of the Molecular Redistribution Reaction of Alkanes with a Dual-Functional Catalyst System, *J. Catalysis* 31, 55-64 (1973) (See also U.S. Pat. No. 6,566,568 to Chen). These techniques have not been widely implemented. Accordingly, there is a need for new ways to convert lower molecular weight alkanes to higher molecular weight alkanes useful as liquid hydrocarbon fuels.

SUMMARY OF THE INVENTION

A first aspect of the present invention is a method of converting at least one first alkane to a mixture of at least one low molecular weight alkane (optionally also including additional lower and/or higher molecular weight alkanes) and at least one high molecular weight alkane, comprising: reacting a first alkane in the presence of dual catalyst system comprising a first catalyst (i.e., a hydrogen transfer catalyst) and a second catalyst (i.e., a metathesis catalyst) to produce a mixture of low and high molecular weight alkanes.

In some embodiments of the foregoing, the invention provides a method of converting at least one low molecular weight alkane and at least one high molecular weight alkane to at least one medium molecular weight alkane, comprising: reacting at least one low molecular weight alkane and at least one high molecular weight alkane in the presence of a dual catalyst system comprising a first catalyst (i.e., a hydrogen transfer catalyst) and a second catalyst (i.e., a metathesis catalyst) to produce said at least one medium molecular weight alkanes.

The first alkane or starting alkane or alkanes can, in some embodiments, be produced by Fischer Tropsch catalysis of a synthesis gas. Fuels such as diesel fuel and gasoline can be produced from the either the high or low molecular weight alkane products (depending upon the molecular weight of the first alkane (e.g., liquid vs. wax product of a Fischer Tropsch reaction).

The reaction step can be carried out in any suitable form, including as a batch reaction or continuous reaction, and as a heterogeneous reaction (that is, with immobilized catalyst), as a homogeneous reaction (that is, with solubilized catalyst), or as a mixed system (that is, with one catalyst immobilized and the other catalyst solubilized).

A second aspect of the invention is a composition comprising, in combination, (i) a hydrogen transfer catalyst immobilized on a solid support; and (ii) a metathesis catalyst immobilized on a solid support (which may be the same as, or different from the solid support on which the hydrogen transfer catalyst is immobilized).

The foregoing and other objects and aspects of the present invention are explained in greater detail in the drawings herein and the specification set forth below.

DETAILED DESCRIPTION OF PREFERRED EMBODIMENTS

Figure 1:
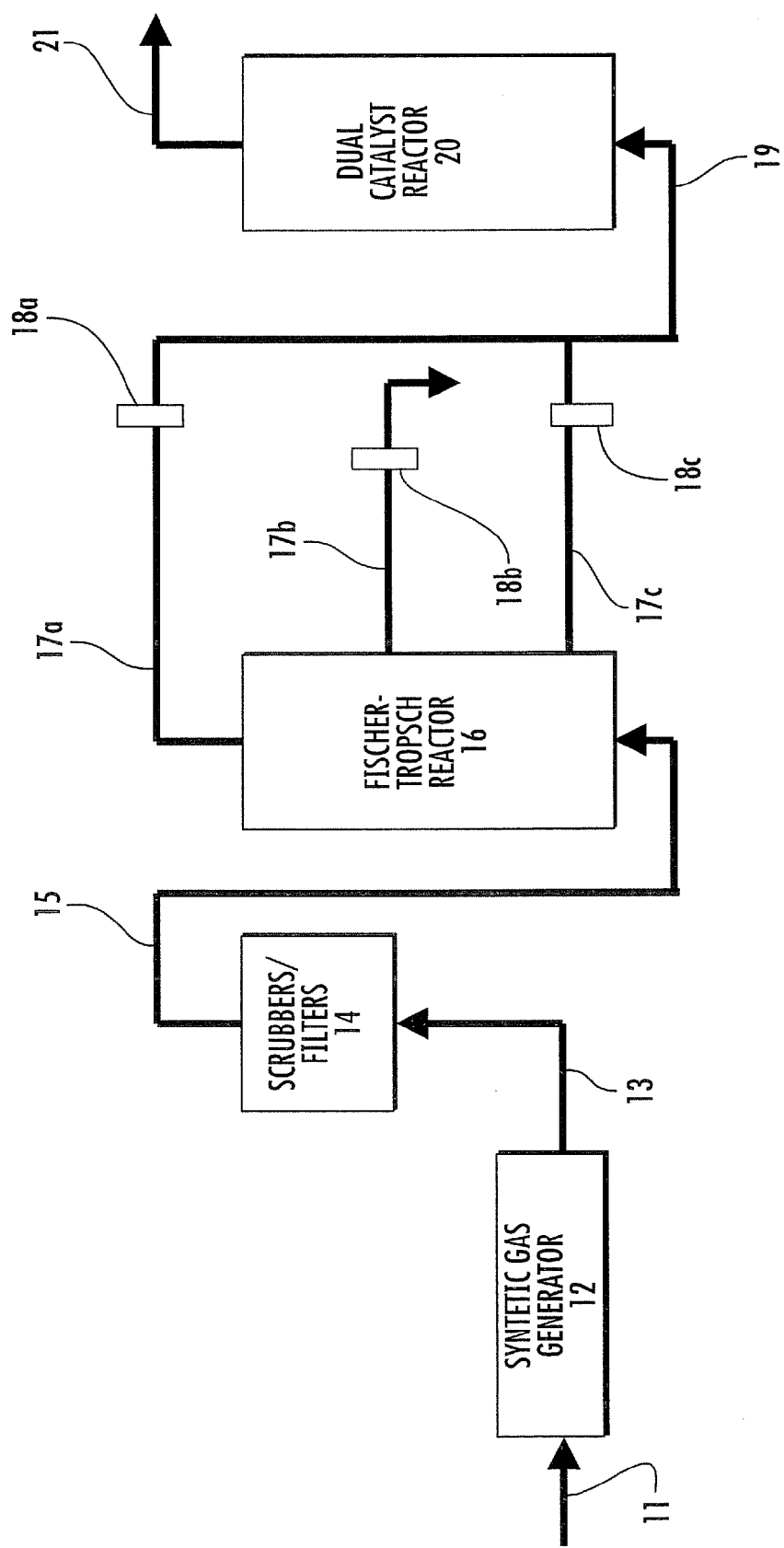
FIG. 1 is a schematic illustration of an apparatus of the present invention.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States patents cited herein are to be incorporated herein by reference in their entirety.

1. First alkane supply. The first alkane used to carry out the present invention can be a single alkane or a mixture of alkanes containing the identified alkane, or range of alkanes, to be reacted. The first alkane can be provided in a hydrocarbon feed composition from any suitable source, in accordance with known techniques such as fractional distillation, cracking, reforming, dehydrogenation, etc (including combinations thereof). One suitable source described further herein, by no means to be taken as limiting of the present invention, is the output of a Fischer-Tropsch reaction system.

The present invention is useful for, among other things, converting the lower molecular weight alkanes produced by a Fischer Tropsch reaction to higher molecular weight alkanes more useful as fuels for internal combustion engines, such as gasoline and diesel fuel.

The production of hydrocarbon compositions comprising alkanes from synthesis gas by Fischer-Tropsch catalysis is well known and may be carried out in accordance with known techniques by reaction of a synthesis gas in the presence of Fischer-Tropsch catalyst in a reactor. Any suitable catalyst can be used, including but not limited to iron and cobalt catalysts. See, e.g., U.S. Pat. No. 6,217,830 to Roberts and Kilpatrick; see also U.S. Pat. Nos. 6,880,635; 6,838,487; 6,201,030; 6,068,760; 5,821,270; 5,817,701; 5,811,363; 5,620,676; and 2,620,347.

The production of synthesis gas from carbonaceous or organic materials such as coal (including coal fines), natural gas, methane, refinery bottoms, vegetative materials such as wood or other biomass, and combinations thereof, is well known and can be carried out in accordance with known techniques. In some embodiments such production involves the partial oxidation of the carbonacous or organic material at elevated temperatures, and optionally elevated pressures, with a limited volume of oxygen, the reaction preferably being carried out in a reactor into which the material is fed, together with additional agents such as steam, carbon dioxide, or various other materials. See e.g., U.S. Pat. No. 4,959,080; see also U.S. Pat. No. 4,805,561.

2. Hydrogen transfer catalysts. Hydrogen transfer catalysts useful for carrying out the present invention are known and described in, for example, U.S. Pat. Nos. 5,744,667; 5,585,530; 5,461,182; 5,227,552 and 3,321,545. Other examples of platinum, rhodium and ruthenium catalysts supported on zeolites and alumina are set forth in R. G. Pellet, *Journal of Catalysis* 177, 40-52 (1998); and S. Naito and M. Tanimoto, *J. Mol. Catal. A: Chemical* 141, 205-214 (1999).

Other examples are iridium catalysts, including but not limited to those described in U.S. Pat. No. 5,780,701; and in:

Goettker-Schnetmann, I., White, P., Brookhart, M., "Iridium Bis(Phosphinite)p-xPCP Pincer Complexes: Highly Active Catalysts for the Transfer Dehydrogenation of Alkanes" J. Am. Chem. Soc. 2004, 126, 1804-1811; Crabtree, R. H.; Mellea, M. F.; Mihelcic, J. M.; Quirk, J. M. "Alkane dehydrogenation by iridium complexes" *J. Am. Chem. Soc.* 1982, 104, 107-13; Felkin, H.; Fillebeen-Khan, T.; Holmes-Smith, R.; Lin, Y. "Activation of carbon-hydrogen bonds in saturated hydrocarbons. The selective, catalytic functionalization of methyl groups by means of a soluble iridium polyhydride system" *Tetrahedron Lett.* 1985, 26, 1999-2000; Burk, M. J.; Crabtree, R. H. "Selective catalytic dehydrogenation of alkanes to alkenes" *J. Am. Chem. Soc.* 1987, 109, 8025-32; Maguire, J. A.; Goldman, A. S. "Efficient Low-Temperature Thermal Functionalization of Alkanes. Transfer-Dehydrogenation Catalyzed by Rh(PMe$_3$)$_2$(CO)Cl in Solution Under High Pressure Dihydrogen Atmosphere" *J. Am. Chem. Soc.* 1991, 113, 6706-6708; Maguire, J. A.; Petrillo, A.; Goldman, A. S. "Efficient Transfer-Dehydrogenation of Alkanes Catalyzed by Rhodium Trimethylphosphine Complexes Under Dihydrogen Atmosphere" *J. Am. Chem. Soc.* 1992, 114, 9492-9498; Gupta, M.; Hagen, C.; Flesher, R. J.; Kaska, W. C.; Jensen, C. M. "A highly active alkane dehydrogenation catalyst: stabilization of dihydrido Rh and Ir complexes by a P-C-P pincer ligand" *Chem. Commun.* 1996, 2083-2084; Wang, K.; Goldman, M. E.; Emge, T. J.; Goldman, A. S. "Transfer-Dehydrogenation of Alkanes Catalyzed by Rhodium(I) Phosphine Complexes" *J. Organomet. Chem.* 1996, 518, 55-68; Gupta, M.; Hagen, C.; Kaska, W. C.; Cramer, R. E.; Jensen, C. M. "Catalytic Dehydrogenation of Cycloalkanes to Arenes by a Dihydrido Iridium P-C-P Pincer Complex" *J. Am. Chem. Soc.* 1997, 119, 840-841; Gupta, M.; Kaska, W. C.; Jensen, C. M. "Catalytic Dehydrogenation of Ethylbenzene and THF by a Dihydrido Iridium P-C-P Pincer Complex" *Chem. Commun.* 1997, 461-462; Xu, W.; Rosini, G. P.; Gupta, M.; Jensen, C. M.; Kaska, W. C.; Krogh-Jespersen, K.; Goldman, A. S. "Thermochemical Alkane Dehydrogenation Catalyzed in Solution Without the Use of a Hydrogen Acceptor" *Chem. Commun.* 1997, 2273-2274; Liu, F.; Pak, E. B.; Singh, B.; Jensen, C. M.; Goldman, A. S. "Dehydrogenation of n-Alkanes Catalyzed by Iridium "Pincer" Complexes. Regioselective Formation of Alpha-Olefins" *J. Am. Chem. Soc.* 1999, 121, 4086-4087; Liu, F.; Goldman, A. S. "Efficient thermochemical alkane dehydrogenation and isomerization catalyzed by an iridium pincer complex" *Chem. Commun.* 1999, 655-656; Jensen, C. M. "Iridium PCP pincer complexes: highly active and robust catalysts for novel homogeneous aliphatic dehydrogenations" *Chem. Commun.* 1999, 2443-2449; Krogh-Jespersen, K.; Czerw, M.; Summa, N.; Renkema, K. B.; Achord, P. D.; Goldman, A. S. "On the Mechanism of (PCP)Ir-catalyzed Acceptorless Dehydrogenation of Alkanes: a Combined Computational and Experimental Study" *J. Am. Chem. Soc.* 2002, 124, 11404-11416; and Zhu, K.; Achord, P. D.; Zhang, X.; Krogh-Jespersen, K.; Goldman, A. S. "Highly Effective Pincer-Ligated Iridium Catalysts for Alkane Dehydrogenation. DFT Calculations of Relevant Thermodynamic, Kinetic, and Spectroscopic Properties" *J. Am. Chem. Soc.* 2004, 126, 13044-13053.

In a preferred embodiment, the hydrogen transfer catalyst is an iridium pincer complex catalyst, such as described above, and also described in U.S. Pat. No. 6,982,305 to Nagy. Examples of such catalysts include but are not limited to compounds of Formula (I):

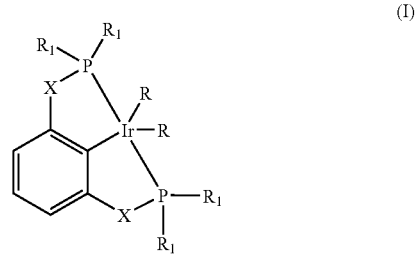

wherein:
each R is independently H or a $C_1$-$C_{30}$ hydrocarbyl radical;
each $R_1$ is independently a $C_1$-$C_{30}$ hydrocarbyl radical; and
each X is independently selected from O and $CH_2$.

3. Olefin metathesis catalysts. Numerous olefin metathesis catalysts, including heterogeneous catalysts and homogeneous catalysts, are known. Specific examples include but are not limited to: Re-based catalysts such as: [≡SiO—Re(≡C$^t$Bu)(═CH$^t$Bu)(CH$_2$$^t$Bu)] (Copéret, C. *New J. Chem.* 2004, 28. 1-10; Thieuleux, C.; Copéret, C.; Dufaud, V.; Marangelli, C.; Kuntz, E.; Basset, J. M. *J. Mol. Catal A: Chemical* 2004, 213, 47-57; Chabanas, M.; Baudouin, A.; Copéret, C.; Basset, J. *J. Am. Chem. Soc.* 2001, 123, 2062); [Re(CO)$_3$OH]$_4$/SiO$_2$ (Copéret, C. *New J. Chem.* 2004, 28. 1-10); Re$_2$O$_7$/mesoporous Al$_2$O$_3$ (Balcar, H.; Hamtil, R.; Zilkova, N.; Cejka, J. *Catal. Lett.* 2004, 97(1-2), 25-29; Oikawa, T.; Ookoshi, T.; Tanaka, T.; Yamamoto, T.; Onaka, M. *Microporous and Mesoporous Materials* 2004, 74, 93-103); Re$_2$(CO)$_{10}$/Al$_2$O$_3$ (Mol, J. C.; Moulijn, J. A. *Adv. Catal.* 1975, 24, 131); Re$_2$O$_7$/Al$_2$O$_3$ (Mol, J. C.; Moulijn, J. A. *Adv. Catal.* 1975, 24, 131; Grubbs, R. H. Alkene and Alkyne Metathesis Reactions. In *Comprehensive Organometallic Chemistry*; Wilkinson, G., Ed. Pergamon Press Ltd.: New York, 1982; p 499; Mol, J. C.; Visser, F. R.; Boelhouwer, C. *J. Catal.* 1970, 17, 114; Satio, K.; Yamaguchi, T.; Tanabe, K. *Bull. Chem. Soc. Jpn.* 1979, 52, 3192); Re$_2$O$_7$/Al$_2$O$_3$/SiO$_2$ (Mol, J. C. *Catal. Today* 1999, 289-299); Re$_2$O$_7$/Al2O$_3$/Mt$_x$O$_y$ (Mt=transition metal) (Nakamura, R.; Echigoya, E. *Chem. Lett.* 1977, 10, 1227); Re$_2$O$_7$/zeolite (Hamdan, H.; Ramli, Z. *Studies in Surface Science and Catalysis* 1997, 957); Re$_2$O$_7$/Al2O$_3$/SnR$_4$ (R=Me, Et, Bu) (Mol, J. C. *Catal. Today* 1999, 289-299; Finkel'shtein, E. Sh.; Ushakov, N. V.; Portnykh, E. B. *J. Mol. Catal.* 1992, 76, 133); CH$_3$ReO$_3$/Al$_2$O$_3$/SiO$_2$ (Herrmann, W. A.; Wagner, W.; Flessner, U. N.; Volkhardt, U.; Komber, H. *Angew. Chem. Int. Ed. Eng.* 1991, 30(12), 1636-1638; Mathew, T. M.; du Plessis, J. A. K.; Prinsloo, J. J. *J. Mol. Catal.* 1999, 148, 157); and ReO$_3$/SiO$_2$ (Tsuda, N.; Fujimori, A. *J. Catal.* 1981, 69, 410); Mo-based catalysts such as: MoO$_3$/HMS (HMS=hexagonal mesoporous silica) (Ookoshi, T.; Onaka, M. *Chem Commun.* 1998, 2399-2400); MoO$_3$/SiO$_2$ (*Olefin Metathesis and Metathesis Polymerization*; Ivin, K. J., Mol, J. C., Eds.; 2$^{nd}$ ed., 1996, p 496); MoO$_3$/Al$_2$O$_3$ (*Olefin Metathesis and Metathesis Polymerization*; Ivin, K. J., Mol, J. C., Eds.; 2$^{nd}$ ed., 1996, p 496; Thomas, R.; Moulijn, J. A. *J. Mol. Catal.* 1982, 15, 157; Gruenert, W.; Stakheev, A. Yu.; Feldhaus, R; Anders, K; Shpiro, E. S.; Minachev, Kh. M. *J. Catal.* 1992, 135, 287; Copéret, C. *New J. Chem.* 2004, 28. 1-10); MoO$_3$/Al$_2$O$_3$/Sn(CH$_3$)$_4$ (Handzlik, J.; Ogonowski, J. *Catal. Lett.* 2002, 83, 287); MoO$_x$/β—TiO$_2$ (Tanaka, K.; Miyahara, K. *Chem. Commun.* 1980, 666); MoO$_3$/TiO$_2$/SnMe$_4$ (Pariya, C.; Jayaprakash, K. N.; Sarkar, A. *Coord. Chem. Rev.* 1998, 168, 1-48); MoO$_3$/CoO/Al$_2$O$_3$ (Grubbs, R. H.; Swetnick, S. J. *J. Mol. Catal.* 1980, 8, 25; Turner, L.; Howman, E. J.; Bradshaw, C. P. C. *J. Catal.* 1967, 7, 269; Alkema, H. J.; Van Helden, R. *Chem. Abstr.* 1968, 69, 95906; Mol, J. C.; Moulijn, J. A. *Adv. Catal.* 1975, 24, 131; Grubbs, R. H. Alkene and Alkyne Metathesis Reactions. In *Comprehensive Organometallic Chemistry*; Wilkinson, G., Ed. Pergamon Press Ltd.: New York, 1982; p 499); MoO$_3$/Cr$_2$O$_3$/Al$_2$O$_3$ (Mol, J. C.; Moulijn, J. A. *Adv. Catal.* 1975, 24, 131); Mo(CO)$_6$/SiO$_2$ (Brenner, A.; Hucul, D. A.; Hardwick, S. J. *Inorg. Chem.* 1979, 18, 1478); Mo(CO)$_6$/γ-Al$_2$O$_3$ (Olsthoorn, A. A.; Moulijn, J. A. *J. Mol. Catal* 1980, 8, 147; Farona, M. F.; Tucker, R. L. *J. Mol. Catal* 1980, 8, 25; Mol, J. C.; Moulijn, J. A. *Adv. Catal.* 1975, 24, 131); (π-C$_3$H$_5$)$_4$Mo/SiO$_2$/Al$_2$O$_3$ (Yermakov, Y. I.; Kuznetzov, B. N.; Grabovski, Y. P.; Startzev, A. N.; Lazutkin, A. M.; Zakharov, V. A.; Lazutkina, A. I. *J. Mol. Catal.* 1976, 1, 93); (π-C$_3$H$_5$)$_4$Mo/Al$_2$O$_3$ (Iwasawa, Y.; Ogasawara, S.; Soma, M. *Chem. Lett.* 1978, 1039); [≡SiO—Mo(≡C$^t$Bu)(CH$_2$$^t$Bu)$_2$] (Copéret, C. *New J. Chem.* 2004, 28. 1-10); [≡SiO—Mo(═NH)(═CH$^t$Bu)(CH$_2$$^t$Bu)] (Copéret, C. *New J. Chem.* 2004, 28. 1-10); Mo(CHCMe$_2$Ph)(N-2,6-$^i$Pr$_2$C$_6$H$_3$)[OCMe(CF$_3$)$_2$]$_2$/MCM-41 (Balcar, H.; Zilkova, N.; Sedlacek, J.; Zednik, J. *J. Mol. Catal.* 2005, 232, 53); and MoCl$_x$/PbMe$_4$/SiCl$_4$ (Bykov, V. I.; Butenko, T. A.; Finkel'shtein, E. Sh. Pat. SU 1664786); W-based catalysts such as WO$_3$/SiO$_2$ (Schubert, M.; Gerlach, T.; Hesse, M.; Stephan, J.; Bohm, V.; Brodhagen, A.; Poplow, F. Pat. U.S. 2004260135); WO$_3$/Al$_2$O$_3$ (De Vries, J. L. K. F.; Pott, G. T. *Rec. Trav. Chim. Pays-Bas* 1977, 96, M115); W/Al2O3/HY zeolite (Huang, S.; Liu, S.; Xin, W.; Bai, J.; Xie, S.; Wang, Q.; Xu, L. *J. Mol. Catal. A: Chemical* 2005, 226, 61-68); (π-C$_4$H$_7$)$_4$W/SiO$_2$ (Startsev A. N.; Kuznetsov, b. N.; Yermakov, Y. I. *React. Kinet. Catal. Lett.* 1976, 3, 321); WO$_3$/SiO$_2$/MgO (Mazurek, H.; Sofranko, J. A. U.S. Pat. No. 4,788,376); W03/ZrO$_2$ (Yoshinaga, Y.; Kudo, M.; Hasegawa, S.; Okuhara, T. *Applied Surface Science* 1997, 121/122 339); H$_3$PW$_{12}$O$_{40}$ (Hudec, P.; Prandova, K. *Collection of Czechoslovak Chemical Communications* 1995, 60(3), 443); (Polystyrylbipyridine) W(CO)$_4$ (Tamagaki, S.; Card, R. J.; Neckers, D. C. *J. Am. Chem. Soc.* 1978, 100, 6635-6639); [≡SiO—W(≡C$^t$Bu)(CH$_2$$^t$Bu)$_2$] (Copéret, C. *New J. Chem.* 2004, 28. 1-10); ($^t$BuO)$_2$W═C$^t$Bu]/SiO$_2$ (Weiss, K.; Lössel, G. *Angew. Chem. Int. Ed. Eng.* 1982, 28(1), 62-64); [(neopentyl)$_2$W═C$^t$Bu]/SiO$_2$ (Weiss, K.; Lössel, G. *Angew. Chem. Int. Ed. Eng.* 1982, 28(1), 62-64); [Cl$_2$W═C$^t$Bu]/SiO$_2$ (Weiss, K.; Lössel, G. *Angew. Chem. Int. Ed. Eng.* 1982, 28(1), 62-64); WCl$_6$/SiO$_2$/1,1,3,3-(CH$_3$)$_4$-disilacyclobutane (Shouvalova, O. V.; Bespalova, N. B.; Nieczypor, P.; Mol, J. C. NATO Science Series, II: Mathematics, Physics and Chemistry (2003), 122 (Novel Metathesis Chemistry), 173); Aryloxy tungsten/NbO$_x$/SiO$_2$/$^i$BuAlCl$_2$ (Verpoort, F.; Bossuyt, A.; Verdonck, L. *Chem. Commun.* 1996, 417); Schrock W carbene/SiO$_2$ (Weiss, K.; Hoffmann, K. *Mathematical and Physical Sciences* 1989 355); [Ru(polymer-CH$_2$OCOCF$_2$CF$_2$CF$_2$COO)(CF$_3$CO$_2$)(═CH-o-$^i$PrOC$_6$H$_4$)(IMesH$_2$) (Krause, Jens O.; Nuyken, Oskar; Wurst, Klaus; Buchmeiser, Michael R. *Chem. Eur. J.* 2004, 10, 777); and a solid-supported phosphine-free ruthenium alkylidene (Connon, S. J.; Blechert, S. *Bioorganic & Medicinal Chemistry Letters* 2002, 12(14) 1873).

In some embodiments Schrock catalysts are preferred as metathesis catalysts. See, e.g., U.S. Pat. Nos. 6,852,900; 6,660,813; 6,538,131; 6,380,420; and 5,942,638.

In some embodiments, Grubb catalysts are less preferred as metathesis catalysts.

In some embodiments, the metathesis catalyst is at least one of, or a mixture of, molybdic acid, ruthenium trichloride, ruthenium trichloride trihydrate, ruthenium tribromide, ruthenium triiodide, tungsten hexachloride, tungsten hexabromide, tungsten hexaiodide, molybdenum chloride, molybdenum bromide, molybdenum iodide, ruthenium oxide, tungsten oxide, tantalum chloride, tantalum bromide, tantalum iodide, tantalum oxide, a tetraalkyl or tetraaryltin complex of a tungsten halide, molybdenum halide, tantalum halide, rhenium halide, ruthenium halide, molybdenum oxide such as a lithium aluminum hydryde activated molybdenum oxide, rhenium oxide, cobalt oxide include cobalt oxide-molybdenum oxide, rhenium pentachloride, rhenium pentabromide, rhenium pentaiodide, trialkyl aluminum and dialkyl aluminum chloride complexes of rhodium halides, tungsten halide, molybdenum halide, ruthenium halide. See, e.g., U.S. Pat. No. 5,324,616; see also U.S. Pat. Nos. 6,727, 396 and 5,672,803.

In some embodiments, such metal catalysts that are free of or do not incorporate organic ligands are preferred.

Particularly preferred olefin methathesis catalysts include, but are not limited to Schrock catalysts, molybdenum catalysts, tungsten oxide catalysts, and rhenium oxide catalysts, which are preferably on a solid support as discussed below.

4. Dual catalyst systems and methods. The present invention is carried out by reacting at least one first alkane as described above in the presence of (i) a first hydrogen transfer catalyst as described above and (ii) a second metathesis catalyst as described above, to produce the mixture of at least one lower molecular weight alkane and at least one higher molecular weight alkane. The conditions of the reaction are not critical, but in general the reacting step is carried out at an elevated temperature (e.g., 50, 100, or 150° C., up to 200, 250 or 300° C., or more, but in some embodiments with a temperature not greater than 300, 250, or 200° C.), for a time of one, five or ten minutes up to one or two hours or more, at atmospheric pressure or an elevated pressure. The reaction may be carried out continuously or as a batch reaction depending upon reactor design, all of which can be implemented in accordance with known techniques. The reaction may be a homogeneous reaction (that is, the catalysts free of a support) or a heterogeneous reaction (that is, the catalysts coupled to or immobilized on a solid support), again in accordance with known techniques.

The first alkane may, in some embodiments, be a linear or branched compound of the formula $C_nH_{2n+2}$ where n is 3-10. The at least one high molecular weight alkane may be a linear or branched compound of the formula $C_mH_{2m+2}$, where m is an integer from 4 to 40.

In other embodiments the first alkane is of a still higher molecular weight (e.g., a Fischer Tropsch wax). In such embodiments the lower molecular weight reaction products can be utilized as a "high molecular weight" alkane in a fuel, and the still higher molecular weight products recycled or subjected to cracking or other suitable reaction.

In some embodiments the first alkane is supplied to the reaction in the form of liquid a Fischer-Tropsch reaction product or a portion thereof. In such embodiments the at least one first alkane is linear, and the alkane is included in a mixed composition comprising both alkanes and alkenes, with the ratio of alkanes to alkenes being relatively high, for example a weight ratio of at least 10:1, 50:1, 100:1 or 200:1 or more.

The reaction is in some embodiments initiated by inclusion or addition of a hydrogen acceptor: that is, is carried out in the presence of a hydrogen acceptor. In some embodiments, the amount of the hydrogen acceptor is preferably not so great as to deleteriously bind to the catalyst and slow the reaction. In such embodiments, the molar ratio of the hydrogen acceptor to said hydrogen transfer catalyst is preferably not greater than 10:1. In some embodiments the catalyst itself may serve as a hydrogen acceptor, e.g., in the case of iridium catalysts such as (PCP)IrPhH, or complexes like (pincer)Ir(ethylene) (where "pincer" refers to polydentate ligands of the type illustrated in the references cited in section 2 above, or other such ligands known in the art).

When included, any suitable hydrogen acceptor can be used. In some embodiments olefin hydrogen acceptors are preferred. Examples of hydrogen acceptors include but are not limited to norbornene, t-butylethylene, ethylene, propene, $CH_2\!\!=\!\!CH(CH_2)_nCH_3$ where n is 1 to 25, etc. Note that the hydrogen acceptor may be exogenously added to the system or inherent in the composition being subject to the reaction (e.g., olefins may already be present in the product of a Fischer-Tropsch reaction).

Where one or the other, or both, catalysts are coupled to or immobilized on a solid support, the support may be porous or nonporous, in any suitable form, and formed from any suitable material such as alumina, silica, titania, kieselguhr, diatomaceous earth, bentonite, clay, zirconia, magnesia, zeolites, carbon black, activated carbon, graphite, fluoridated carbon, organic polymers, metals, metal alloys, and combinations thereof, in accordance with known techniques. See, e.g., U.S. Pat. No. 6,908,873. Catalysts including iridium pincer catalysts can be immobilized in accordance with known techniques, with one example of an immobilized iridium pincer catalyst complex being represented by Formula (II):

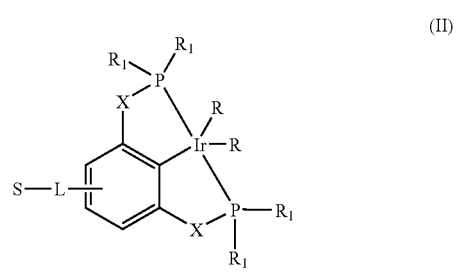

wherein:
each R is independently H or a $C_1$-$C_{30}$ hydrocarbyl radical;
each $R_1$ is independently a $C_1$-$C_{30}$ hydrocarbyl radical;
each X is independently selected from O and $CH_2$;
L is any suitable linking group, including aromatic, aliphatic and mixed aromatic and aliphatic linking groups; and
S is a solid support such as described above.

In some embodiments, the production of branched higher molecular weight alkanes is advantageously minimized, such that the at least one higher molecular weight alkane produced by the reaction comprises a mixture at a Molar ratio of linear alkanes to branched alkanes of at least 500:1, and more preferably at a Molar ratio of at least 1000:1.

In some embodiments, wherein the hydrogen transfer catalyst is immobilized on a solid support and the reaction is carried out in a solvent, the method may further comprises the step of separating free hydrogen transfer catalyst from said solvent. Such separating may be carried out by any suitable means, such as by adding an additional an adsorption agent to the solvent to adsorb otherwise free hydrogen transfer catalyst. Any suitable adsorption agent may be used, including but not limited to alumina, silica, titania, kieselguhr, diatomaceous earth, bentonite, clay, zirconia, magnesia, zeolites, carbon black, activated carbon, graphite, fluoridated carbon, organic polymers, metals, metal alloys, and combinations thereof. Without wishing to be bound to any particular theory, it is believed that the added free support adsorb otherwise free hydrogen transfer catalyst that would otherwise interfere with the activity of the (preferably also immobilized) metathesis catalyst.

One embodiment of the method of the present invention is schematically illustrated in Scheme 1 below, with an iridium catalyst as the hydrogen transfer catalyst.

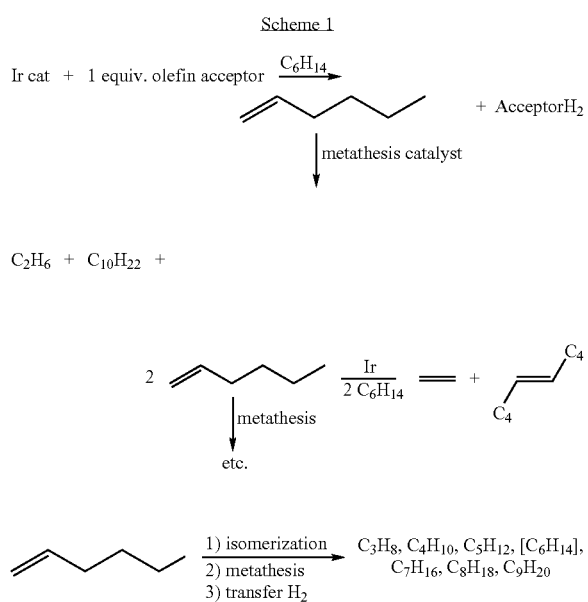

5. Additional process steps, apparatus and utility. Lower and higher molecular weight alkanes, particularly higher molecular weight liquid alkanes, produced by the methods of the present invention can be utilized as fuels and solvents in accordance with known techniques, and/or further processed by known techniques to produce fuels therefrom. For example, the higher molecular weight alkanes can be separated from the lower molecular weight alkanes by distillation, the higher molecular weight alkanes utilized as fuels, and the lower molecular weight alkanes utilized per se or returned and recycled for further synthesis. Additional processing techniques such as reforming, blending with other hydrocarbons or other refinery streams, and/or the addition of additives (e.g., oxygenates such as MTBE, ethanol, ETBE, etc; fuel adjuncts such as ignition improvers, stability improvers, corrosion inhibitors, detergent additives, cold flow improvers, combustion improvers, luminosity reducers/radiation quenchers, antimicrobial/antifungal adjuncts, antistats, and other conventional jet fuel adjuncts and mixtures thereof), to produce liquid hydrocarbon fuels such as gasoline (or "petrol") or diesel fuel, can also be carried out if desired, all in accordance with known techniques. See, e.g., U.S. Pat. Nos. 6,896,708 and 6,880,635; see also U.S. Pat. Nos. 6,884,916; 6,881,235; 6,863,802; 6,858,047; 6,767,372; 6,565,617; 6,551,502; 6,533,924; 6,527,816; 6,540,797; 6,890,364; and 6,833,064.

An apparatus for carrying out a method of the invention is schematically illustrated in FIG. 1. Carbonaceous or organic material such as coal, methane, natural gas, or biomass is supplied via line 11 to the synthesis gas generator 12, where it is partially oxidized by air, pure oxygen, steam and/or methane to produce synthesis gas, all of which may be carried out in accordance with known techniques. The synthesis gas exits generator 12 by line 13, and is then (optionally but preferably) at least partially cleaned of undesired compounds such as HCN, $NH_3$ and/or sulfur gases by scrubbers and/or filters 14. Any suitable scrubber, filter, or cleaning system may be utilized. See, e.g., U.S. Pat. Nos. 2,863,527; 4,088,735; 4,155,985; 3,975,178; 3,956,460; 4,007,129; 4,058,376; 4,189,307; and 4,271,133.

Synthesis gas exits the optional filters and/or scrubbers 14 by line 15 and enters Fischer-Tropsch reactor 16. Any suitable Fischer-Tropsch reactor may be utilized including slurry and non-slurry (fixed bed or fluidized bed) reactors (e.g., circulating fluidized bed reactors, ebulating or fixed fluidized bed reactors, slurry-phase bubbling bed reactors or slurry bubble-column reactors, etc.). The reactors can contain any suitable Fischer-Tropsch catalyst. Particular examples of suitable reactors and catalysts are set forth above and in the patents cited above and incorporated herein by reference. One or more feed lines 17a, 17B, and 17C containing the reaction product of the Fischer-Tropsch reaction leaves the reactor (e.g., the light fraction via line 17a, the medium fraction via line 17b, and the heavy fraction such as wax via line 17c). Each feed line 17a-17c may be controlled by a valve 18a-18c, and hence provides for controlled input to dual catalyst reactor 20 via line 19. (Alternatively, lines 17a-17c or any combination thereof may proceed directly to reactor 20 rather than feed through a common line 19).

For example, a medium molecular weight fraction of the Fischer-Tropsch reactor may be withdrawn via line 18b and the dual catalyst reactor 20 may be supplied with either: a light weight fraction of the F-T reaction via line 17a and valve 18a; a heavy weight or wax fraction of the F-T reaction via line 17c and valve 18c; or a mixture of light and heavy weight fractions in any suitable proportion via a combination thereof.

The dual catalyst reactor 20 may be of any suitable format or configuration, such as those described in connection with the Fischer-Tropsch reactor above. Product of the dual catalyst reaction is then taken by line 21 for use as a fuel, or for any other suitable purpose.

It will be appreciated that the apparatus of FIG. 1 is presented in schematic form. Additional components such as return lines for recycling output from a reactor for further reaction, separation or distillation units for separating the components of a reaction product for further processing, additional feed lines for adding or blending additional components or additives, etc., can also be included, as will be apparent to those skilled in the art. Lines can be consolidated or valves replaced or repositioned, separation can be achieved by distillation rather than fractionation, etc.

The dual catalyst reactions described herein convert a first alkane to alkanes of both higher and lower molecular weight ("higher" and "lower" being relative to the first alkane). In the fuel synthesis methods described above it is generally suggested that the higher molecular weight products of the dual catalyst reaction are desired. However, Fischer-Tropsch reactions also produce a wax product of still higher molecular weight, and when such waxes are further processed by the reactions of the invention, it is the lower molecular weight products utilized to make fuels and the higher molecular weight products utilized for recycling (or other purposes).

Thus the present invention also provides a method of making a liquid hydrocarbon fuel, such as diesel fuel or gasoline, from a synthesis gas by the Fischer-Tropsch reaction, wherein said fuel comprises at least one high molecular weight alkane, wherein at least a portion of the product of said Fischer Tropsch reaction comprises a wax, and wherein said wax is of still higher molecular weight than said high molecular weight alkane, in which at least a portion of said wax is converted to said at least one high molecular weight alkane by reacting said wax in the presence of a dual catalyst system comprising: (i) a hydrogen transfer catalyst and (ii) a metathesis catalyst to produce said at least one high molecular weight alkane (here the "high molecular weight alkane" is the lower molecular weight product of the dual catalyst reaction).

Note that very low molecular weight alkanes produced from the F-T reaction can also be supplied to the dual catalyst system to aid in the production of the lower molecular weight alkanes (or "medium" molecular weight alkanes, relative to the very low molecular weight alkanes) from the high molecular weight waxes.

Apparatus as described in FIG. 1 above can be modified to carry out such methods by configuring them to draw the wax product from the Fischer Tropsch reactor 16 to the dual catalyst reactor 18.

While the present invention has been described with reference to single alkanes such as "first alkane", "low molecular weight alkane", "high molecular weight alkane" "wax", and alkanes of particular chain lengths, it will be appreciated that in most embodiments of the invention the product alkanes, and in many embodiments the reactant alkanes represent a distribution of multiple alkanes of different carbon number (the majority of which may be within the range indicated) rather than a single compound. Thus, where an alkane is identified by a chain length or range of chain lengths herein, the alkane may be treated (for the purpose of the instant description) as: (i) a single alkane of the identified chain length (alone or in combination with others), or (ii) a mixture of multiple alkanes having either a mean or median chain length corresponding to the identified chain length.

The present invention is described in the following non-limiting examples. In these examples, all manipulations were carried out using standard Schlenk and glovebox techniques. Argon was purified by passage through columns of BASF R3-11 (Chemalog) and 4 Å molecular sieves. Toluene and pentane were passed through columns of activated alumina. Hexane was purchased from Aldrich, dried over $CaH_2$, degassed via several freeze-pump-thaw cycles, and stored under argon. Anhydrous decane was purchased from Aldrich, degassed, and stored under argon. Ammonium perrhenate was purchased from Aldrich and used as received. Gamma-Alumina and $[Mo(C_{10}H_{12})(C_{12}H_{17}N)[OC(CH_3)(CF_3)_2]_2$ were purchased from Strem and used as received. $\{C_6H_3\text{-}2,6\text{-}[OP(t\text{-}Bu)_2]_2\}Ir(H)(Cl)$, $\{C_6H_3\text{-}2,6\text{-}[OP(t\text{-}Bu)_2]_2\}Ir(H)_2$, $\{C_6H_3\text{-}2,6\text{-}[CH_2P(t\text{-}Bu)_2]_2\}Ir(H)_2$, $\{4\text{-}OMe\text{-}C_6H_2\text{-}2,6\text{-}[CH_2P(t\text{-}Bu)_2]_2\}Ir(H)_2$, and $\{4\text{-}OMe\text{-}C_6H_2\text{-}2,6\text{-}[CH_2P(i\text{-}Pr)_2]_2\}Ir(H)_2$ were prepared according to literature procedures (Gottker-Schnetmann, I.; White, P.; Brookhart, M. *J. Am. Chem. Soc.* 2004, 126, 1804-1811; Gottker-Schnetmann, I.; White, P. S.; Brookhart, M. *Organometallics* 2004, 23, 1766-1776; Gupta, M.; Hagen, C.; Flesher, R. J.; Kaska, W. C.; Jensen, C. M. *Chem. Commun.* 1996, 17, 2083-2084; Mohammad, H. A. Y.; Grimm, J. C.; Eichele, K.; Mack, H.-G.; Speiser, B.; Novak, F.; Quintanilla, M. G.; Kaska, W. C.; Mayer, H. A. *Organometallics* 2002, 21, 5775-5784; Zhu, K.; Achord, P. D.; Zhang, X.; Krogh-Jespersen, K.; Goldman, A. S. *J. Am. Chem. Soc.* 2004, 126, 13044-13053. NMR spectra were recorded on Bruker DRX 400 and AMX 300 MHz instruments and are referenced to residual protio solvent. $^{31}P\{^1H\}$ NMR chemical shifts are referenced to an external 85% $H_3PO_4$ standard. GC analysis was performed on an Agilent 6850 Series GC with a dimethylpolysiloxane column (Agilent HP-1).

Example 1

Synthesis of $\{C_6H_3\text{-}2,6\text{-}[OP(t\text{-}Bu)_2]_2\}Ir(C_2H_4)$ $\{C_6H_3\text{-}2,6\text{-}[OP(t\text{-}Bu)_2]_2\}Ir(H)(Cl)$ (1.5 g, 2.4 mmol) and NaO-t-Bu (277 mg, 2.89 mmol) were weighed into a flame-dried Schlenk flask and put under a flow of argon. Toluene (40 mL) was added to the flask via syringe, and the resulting suspension was stirred for 10 min at room temperature. Ethylene was bubbled through the solution for 1-2 hours. The solution was cannula-filtered through a pad of Celite, volatiles were evaporated under vacuum, and the resulting red solid was dried under vacuum overnight to give 867 mg (59% yield) of pure product. $^1H$ NMR ($C_6D_6$): δ 1.24 (t, J=6.8 Hz, 36H), 3.10 (t, J=2.4 Hz, 4H), 6.91-6.94 (m, 2H), 7.01-7.06 (m, 1H). $^{13}C$ NMR ($C_6D_6$): δ28.93 (m, 12C), 36.13 (s, 2C), 41.92 (t, J=11.2 Hz, 4C), 103.98 (t, J=6.0 Hz, 2C), 127.45 (s), 145.19 (t, J=8.5 Hz), 168.17 (t, J=8.4 Hz, 2C). $^{31}P\{^1H\}$ NMR ($C_6D_6$): δ 181.7 (s). Anal. Calc'd for $C_{24}H_{43}O_2P_2Ir$; C, 46.65; H, 7.03. Found: C, 46.64; H, 7.15.

Example 2

Synthesis of $\{C_6H_3\text{-}2,6\text{-}[OP(t\text{-}Bu)_2]_2\}Ir(C_2H_4)$ Supported on Alumina $\{C_6H_3\text{-}2,6\text{-}[OP(t\text{-}Bu)_2]_2\}Ir(C_2H_4)$ (150 mg, 0.242 mmol) and γ-alumina (2.50 g, 24.5 mmol; previously calcined at 500° C.) were weighed into a Schlenk flask and put under a flow of argon. Pentane (10 mL) was added via syringe, and the suspension was stirred gently at room temperature for 2 hours. The rust-colored solid was filtered and washed with pentane until the washings were colorless, and was dried under vacuum to yield 2.49 g (94% yield) of supported catalyst.

Example 3

Synthesis of $Re_2O_7$ Supported on Alumina

The following procedure was adapted from literature procedure (Mol, J. C. *Catal. Today* 1999, 51, 289-299). In a vial, 1.20 g (4.47 mmol) of $NH_4Re_2O_4$ was dissolved in 30 mL distilled water. This solution was added to 10 g (98 mmol) of γ-$Al_2O_3$. The suspension was swirled by hand for about a minute, then allowed to stand undisturbed at room temperature for 30 min. This cycle of swirling and standing was repeated until all of the water was absorbed by the alumina. The solid was dried in a 120° C. oven overnight, then calcined at 550° C. for 3 hours under a flow of $O_2$ and for 3 hours under a flow of Ar. After cooling to room temperature under an Ar flow, the solid was brought into the drybox and stored there.

Examples 4-5

Procedures for Reactions with Homogeneous Transfer Dehydrogenation and Olefin Metathesis Catalysts

Example 4

Alkane Metathesis: $\{C_6H_3\text{-}2,6\text{-}[OP(t\text{-}Bu)_2]_2\}Ir(C_2H_4)$ and Schrock's Catalyst $[Mo(C_{10}H_{12})(C_{12}H_{17}N)][OC(CH_3)(CF_3)_2]_2$ A flask was charged with 13 mg (0.021 mmol) of $\{C_6H_3\text{-}2,6\text{-}[OP(t\text{-}Bu)_2]_2\}Ir(C_2H_4)$, 2.7 μL (0.021 mmol) of tert-butyl ethylene as hydrogen acceptor, 26 mg (0.034 mmol) of the hexafluorinated Schrock catalyst $([Mo(C_{10}H_{12})(C_{12}H_{17}N)][OC(CH_3)(CF_3)_2]_2)$, 2 mL (15.3 mmol) of hexane, and 8.8 μL (0.063 mmol) of mesitylene as internal standard. The flask was sealed tightly with a teflon plug under an argon atmosphere, and the solution stirred in a 125° C. oil bath. Periodically, the flask was removed from the bath and cooled. An aliquot was removed from the flask, and analyzed by GC. Turnover numbers were calculated for each aliquot. Data are given in the Tables below.

Example 4a

With 1 Equiv of Added Hydrogen Acceptor

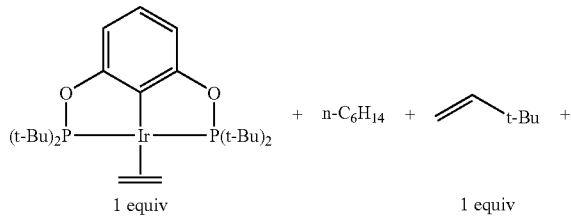

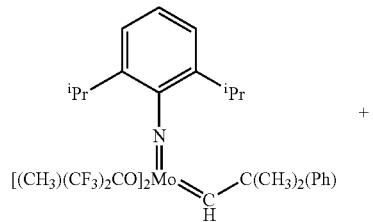

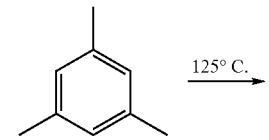

| Time (d) | $C_7$ | $C_8$ | $C_9$ | $C_{10}$ | $C_{11}$ | $C_{12}$ | $C_{13}$ | $C_{14}$ | $C_{15}$ | Total Turnovers |
|---|---|---|---|---|---|---|---|---|---|---|
| 1 | 11.6 | 6.8 | 6.3 | 3.8 | 1.8 | 0.32 | 0.14 | 0.08 | 0 | 59 |
| 2 | 22.1 | 12.2 | 9.8 | 6.3 | 2.7 | 0.68 | 0.33 | 0.17 | 0.06 | 105 |
| 4 | 25.4 | 14.0 | 13.5 | 8.3 | 3.5 | 1.1 | 0.58 | 0.37 | 0.12 | 128 |
| 6 | 28.3 | 15.3 | 14.9 | 9.1 | 3.9 | 1.3 | 0.74 | 0.51 | 0.17 | 142 |
| 8 | 29.3 | 15.8 | 15.6 | 9.4 | 4.0 | 1.4 | 0.80 | 0.54 | 0.18 | 147 |
| 11 | 31.2 | 16.7 | 16.5 | 9.9 | 4.2 | 1.5 | 0.88 | 0.60 | 0.20 | 156 |

Total turnovers = $[(C_7 \times C_8 \times C_9 \times C_{10}) \times 2] + C_{11}$ and up

Example 4b

With 0 Equiv of Added Hydrogen Acceptor

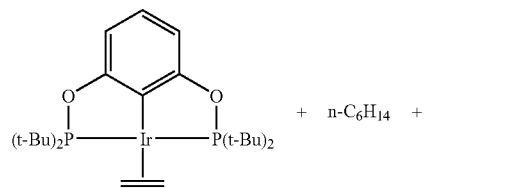
+ n-C$_6$H$_{14}$ +

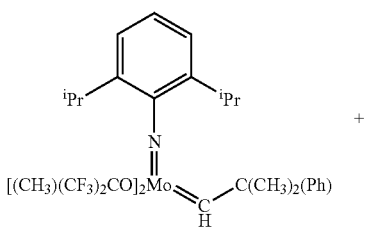
+

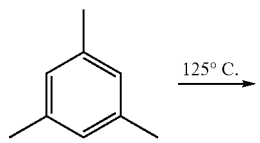
$\xrightarrow{125° C.}$

| Time (d) | C$_7$ | C$_8$ | C$_9$ | C$_{10}$ | C$_{11}$ | C$_{12}$ | C$_{13}$ | C$_{14}$ | C$_{15}$ | Total Turnovers |
|---|---|---|---|---|---|---|---|---|---|---|
| 1 | 29.1 | 15.6 | 15.3 | 10.1 | 4.3 | 1.3 | 0.76 | 0.53 | 0.19 | 147 |
| 2 | 30.2 | 16.1 | 15.7 | 10.2 | 4.3 | 1.3 | 0.79 | 0.54 | 0.19 | 152 |
| 4 | 36.1 | 17.5 | 16.2 | 10.1 | 4.3 | 1.3 | 0.80 | 0.56 | 0.20 | 167 |

Total turnovers = [(C$_7$ × C$_8$ × C$_9$ × C$_{10}$) × 2] + C$_{11\ and\ up}$.

Example 5

Alkane Metathesis: {C$_6$H$_3$-2,6-[OP(t-Bu)$_2$]$_2$}Ir(H)$_2$ and Schrock's Catalyst [Mo(C$_{10}$H$_{12}$)(C$_{12}$H$_{17}$N) [OC(CH$_3$)(CF$_3$)$_2$]$_2$ The same procedure described above was followed with the following reagents: 13 mg (0.021 mmol) of {C$_6$H$_3$-2,6-[OP(t-Bu)$_2$]$_2$}Ir(H)$_2$, 5.4 μL (0.042 mmol) of tert-butyl ethylene, 26 mg (0.034 mmol) of the hexafluorinated Schrock catalyst ([Mo(C$_{10}$H$_{12}$)(C$_{12}$H$_{17}$N)[OC(CH$_3$)(CF$_3$)$_2$]$_2$), 2 mL (15.3 mmol) of hexane, and 8.8 μL (0.063 mmol) of mesitylene. Data is given in the Table below.

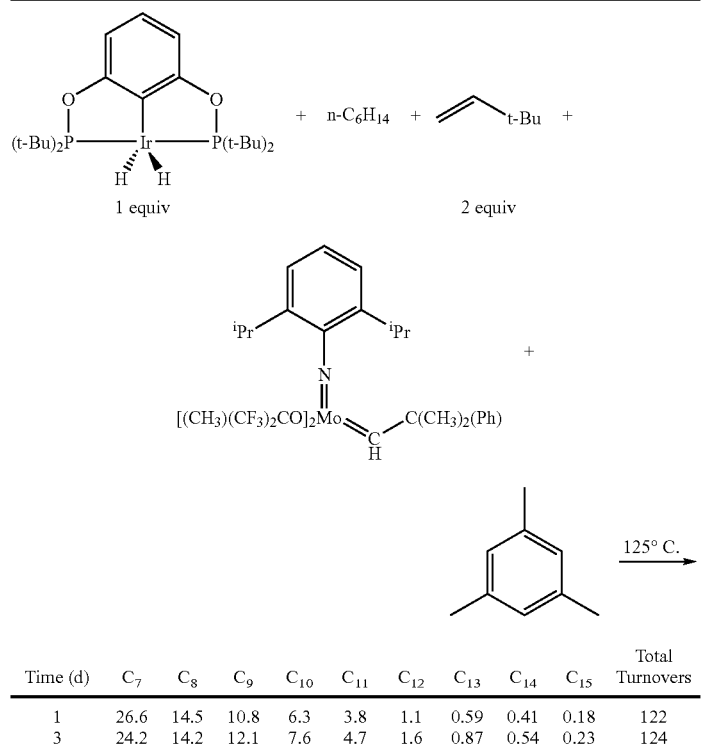

| Time (d) | $C_7$ | $C_8$ | $C_9$ | $C_{10}$ | $C_{11}$ | $C_{12}$ | $C_{13}$ | $C_{14}$ | $C_{15}$ | Total Turnovers |
|---|---|---|---|---|---|---|---|---|---|---|
| 1 | 26.6 | 14.5 | 10.8 | 6.3 | 3.8 | 1.1 | 0.59 | 0.41 | 0.18 | 122 |
| 3 | 24.2 | 14.2 | 12.1 | 7.6 | 4.7 | 1.6 | 0.87 | 0.54 | 0.23 | 124 |

Total turnovers = $[(C_7 \times C_8 \times C_9 \times C_{10}) \times 2] + C_{11}$ and up.

Examples 6-10

Procedures for Reactions with a Homogeneous Transfer Dehydrogenation Catalyst and a Heterogeneous Olefin Metathesis Catalyst Decane was used for reactions with $Re_2O_7/Al_2O_3$ as metathesis catalyst (Examples 6-11); alkane products up to $C_{34}$ were observed in some cases. For the sake of brevity only the total turnover numbers are reported, along with the range of alkane products observed.

Example 6

Alkane Metathesis: $\{C_6H_3\text{-}2,6\text{-}[OP(t\text{-}Bu)_2]_2\}Ir(C_2H_4)$ and $Re_2O_7/Al_2O_3$ A flask was charged with 13 mg (0.021 mmol) of $\{C_6H_3\text{-}2,6\text{-}[OP(t\text{-}bu)_2]_2\}Ir(C_2H_4)$, 2.7 μL (0.021 mmol) of tert-butyl ethylene as hydrogen acceptor, 535 mg of $Re_2O_7$ supported on alumina (6% Re by weight), 2.5 mL (12.8 mmol) of decane, and 10.2 mg (0.063 mmol) of hexamethylbenzene as internal standard. The iridium complex immediately adsorbed itself onto the $Re_2O_7$ alumina support, as observed by the colorless solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Data are given in the Tables below.

Example 6a

With 1 Equiv of Added Hydrogen Acceptor

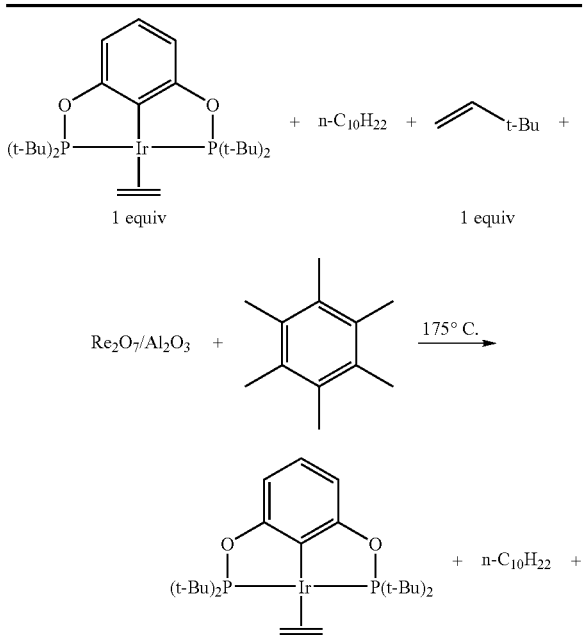

| Time (d) | Alkanes Observed by GC | Total Turnovers |
|---|---|---|
| 0.75 | $C_5$–$C_{21}$ | 33 |
| 3 | $C_5$–$C_{23}$ | 90 |

-continued

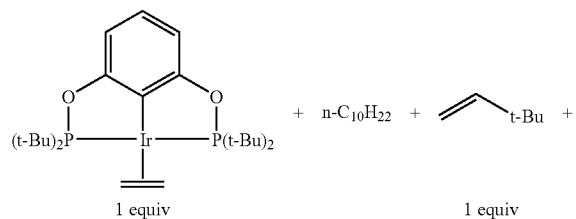

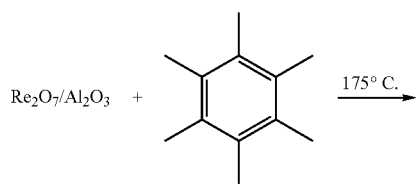

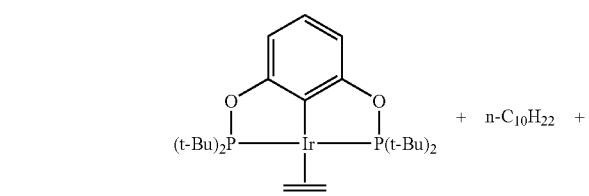

| Time (d) | Alkanes Observed by GC | Total Turnovers |
|---|---|---|
| 5 | $C_5$–$C_{23}$ | 100 |
| 6 | $C_5$–$C_{23}$ | 104 |

Total turnovers = $C_7 + C_8 + C_9 + C_{11} + C_{12} + C_{13} + [(C_{14} \times C_{15} \times C_{16} \times C_{17} \times C_{18}) \times 2] + C_{19}$ and up Example 6b With 0 Equiv of Added Hydrogen Acceptor

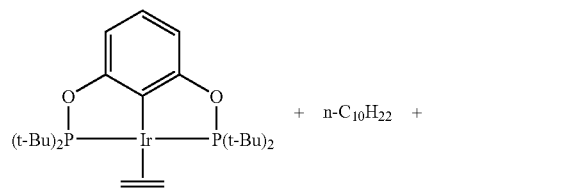

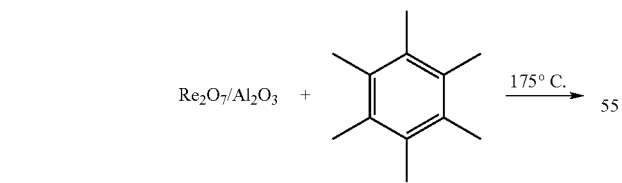

| Time (d) | Alkanes Observed by GC | Total Turnovers |
|---|---|---|
| 0.75 | $C_5$–$C_{21}$ | 42 |
| 3 | $C_5$–$C_{23}$ | 84 |
| 5 | $C_5$–$C_{23}$ | 104 |
| 6 | $C_5$–$C_{23}$ | 118 |

Total turnovers = $C_7 + C_8 + C_9 + C_{11} + C_{12} + C_{13} + [(C_{14} \times C_{15} \times C_{16} \times C_{17} \times C_{18}) \times 2] + C_{19}$ and up Example 7

Figure 2:
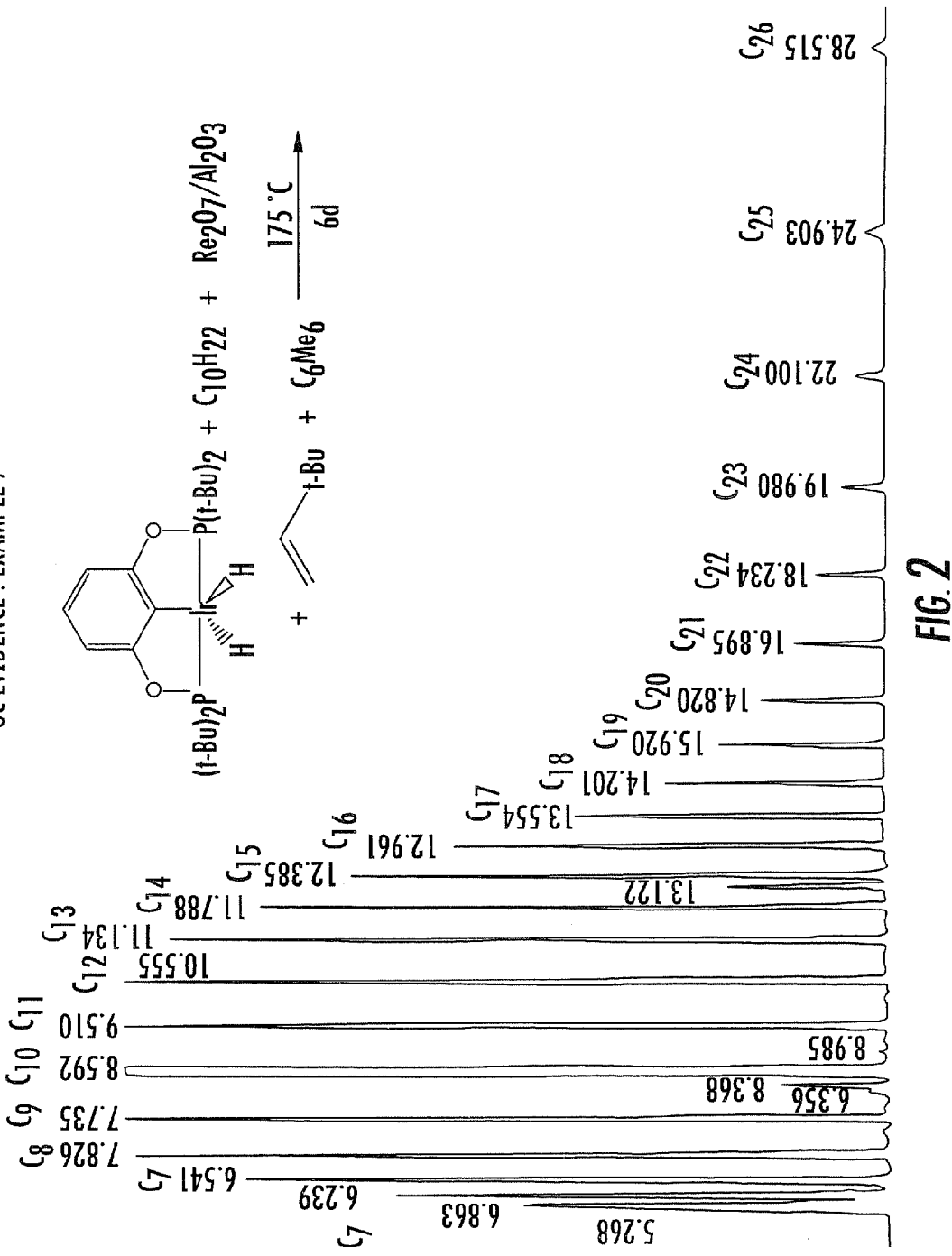
FIG. 2 is a gas chromatogram of the reaction product of the process of Example 7, illustrating the presence of, and hence the production of, higher molecular weight alkanes.

Alkane Metathesis: $\{C_6H_3\text{-}2,6\text{-}[OP(t\text{-}Bu)_2]_2\}Ir(H)_2$ and $Re_2O_7/Al_2O_3$ The same procedure described above was followed with the following reagents: 13 mg (0.021 mmol) of $\{C_6H_3\text{-}2,6\text{-}[OP(t\text{-}Bu)_2]_2\}Ir(H)_2$, 5.4 μL (0.042 mmol) of tert-butyl ethylene, 535 mg of $Re_2O_7$ supported on alumina (6% Re by weight), 2.5 mL (12.8 mmol) of decane, and 10.2 mg (0.063 mmol) of hexamethylbenzene. Data are given in FIG. 2 below and the following Table.

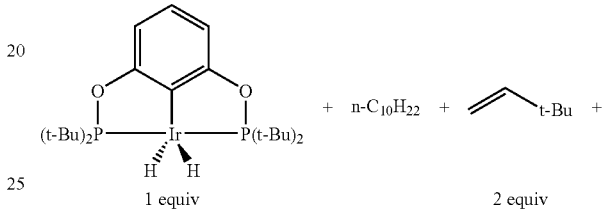

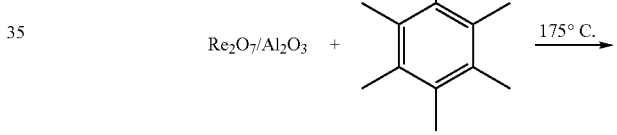

| Time (d) | Alkanes Observed by GC | Total Turnovers |
|---|---|---|
| 0.75 | $C_5$–$C_{25}$ | 41 |
| 3 | $C_5$–$C_{26}$ | 105 |
| 6 | $C_5$–$C_{26}$ | 134 |
| 11 | $C_5$–$C_{26}$ | 168 |

Total turnovers = $C_7 + C_8 + C_9 + C_{11} + C_{12} + C_{13} + [(C_{14} \times C_{15} \times C_{16} \times C_{17} \times C_{18}) \times 2] + C$.and up Example 8

Alkane Metathesis: $\{C_6H_3\text{-}2,6\text{-}[CH_2P(t\text{-}Bu)_2]_2\}Ir(H)_2$ and $Re_2O_7/Al_2O_3$ The same procedure described above was followed with the following reagents: 13.5 mg (0.0230 mmol) of $\{C_6H_3\text{-}2,6\text{-}[CH_2P(t\text{-}Bu)_2]_2\}Ir(H)_2$, 5.4 μL (0.042 mmol) of tert-butyl ethylene, 535 mg of $Re_2O_7$ supported on alumina (6% Re by weight), 2.5 mL (12.8 mmol) of decane, and 10.2 mg (0.063 mmol) of hexamethylbenzene.

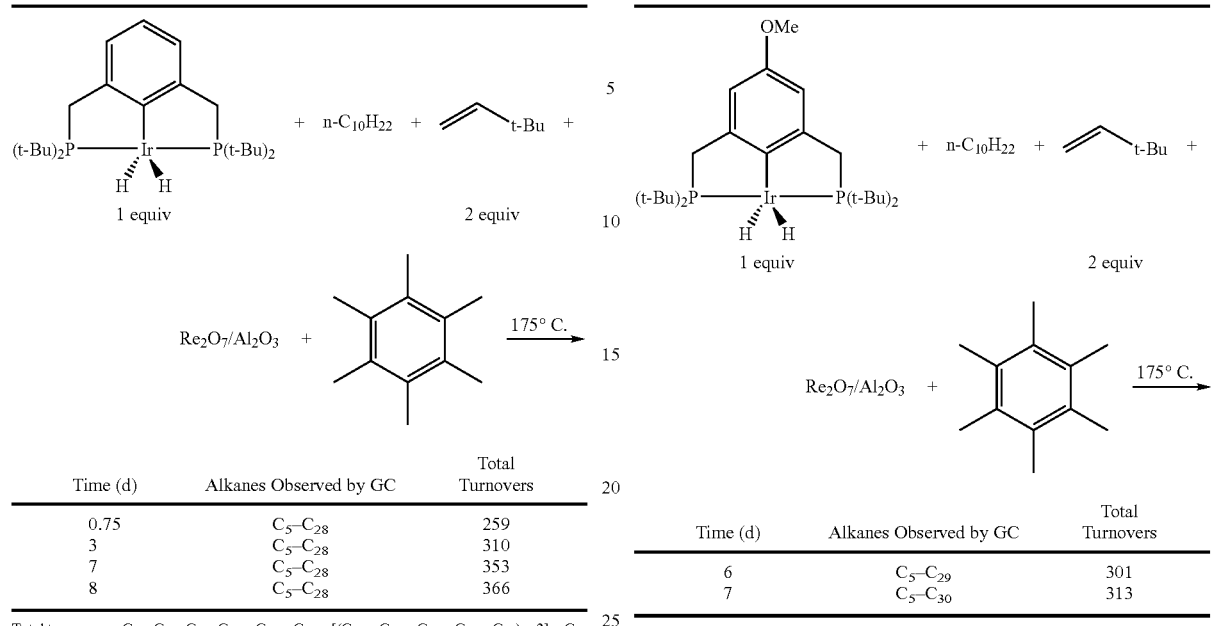

| Time (d) | Alkanes Observed by GC | Total Turnovers |
|---|---|---|
| 0.75 | $C_5$–$C_{28}$ | 259 |
| 3 | $C_5$–$C_{28}$ | 310 |
| 7 | $C_5$–$C_{28}$ | 353 |
| 8 | $C_5$–$C_{28}$ | 366 |

Total turnovers = $C_7 + C_8 + C_9 + C_{11} + C_{12} + C_{13} + [(C_{14} \times C_{15} \times C_{16} \times C_{17} \times C_{18}) \times 2] + C_{19}$ and up

| Time (d) | Alkanes Observed by GC | Total Turnovers |
|---|---|---|
| 6 | $C_5$–$C_{29}$ | 301 |
| 7 | $C_5$–$C_{30}$ | 313 |

Total turnovers = $C_7 + C_8 + C_9 + C_{11} + C_{12} + C_{13} + [(C_{14} \times C_{15} \times C_{16} \times C_{17} \times C_{18}) \times 2] + C_{19}$ and up.

Example 9

Alkane Metathesis {4-OMe-$C_6H_2$-2,6-[$CH_2P$(t-Bu)$_2$]$_2$}Ir(H)$_2$ and Re$_2$O$_7$/Al$_2$O$_3$ The same procedure described above was followed with the following reagents: 14.5 mg (0.0235 mmol) of {4-OMe-$C_6H_2$-2,6-[$CH_2P$(t-Bu)$_2$]$_2$}Ir(H)$_2$, 5.4 μL (0.042 mmol) of tert-butyl ethylene, 535 mg of Re$_2$O$_7$ supported on alumina (6% Re by weight), 2.5 mL (12.8 mmol) of decane 10.2 mg (0.063 mmol) of hexamethylbenzene. Data are given in the Table below.

Example 10

Alkane Metathesis: {4-OMe-$C_6H_2$-2,6-[$CH_2P$(i-Pr)$_2$]$_2$}Ir(H)$_2$ and Re$_2$O$_7$/Al$_2$O$_3$ The same procedure described above was followed with the following reagents: 12.1 mg (0.0215 mmol) of {4-OMe-$C_6H_2$-2,6-[$CH_2P$(i-Pr)$_2$]$_2$}Ir(H)$_2$, 5.4 μL (0.042 mmol) of tert-butyl ethylene, 535 mg of Re$_2$O$_7$ supported on alumina (6% Re by weight), 2.5 mL (12.8 mmol) of decane, and 10.2 mg (0.063 mmol) of hexamethylbenzene. Data is given in the Table below.

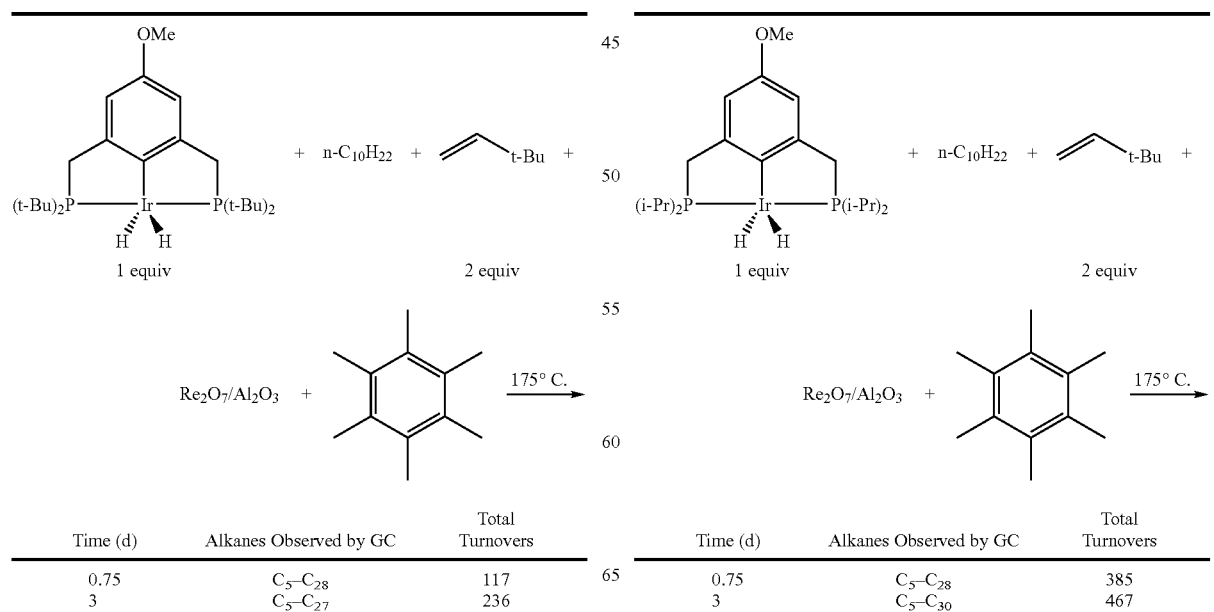

| Time (d) | Alkanes Observed by GC | Total Turnovers |
|---|---|---|
| 0.75 | $C_5$–$C_{28}$ | 117 |
| 3 | $C_5$–$C_{27}$ | 236 |

| Time (d) | Alkanes Observed by GC | Total Turnovers |
|---|---|---|
| 0.75 | $C_5$–$C_{28}$ | 385 |
| 3 | $C_5$–$C_{30}$ | 467 |

-continued

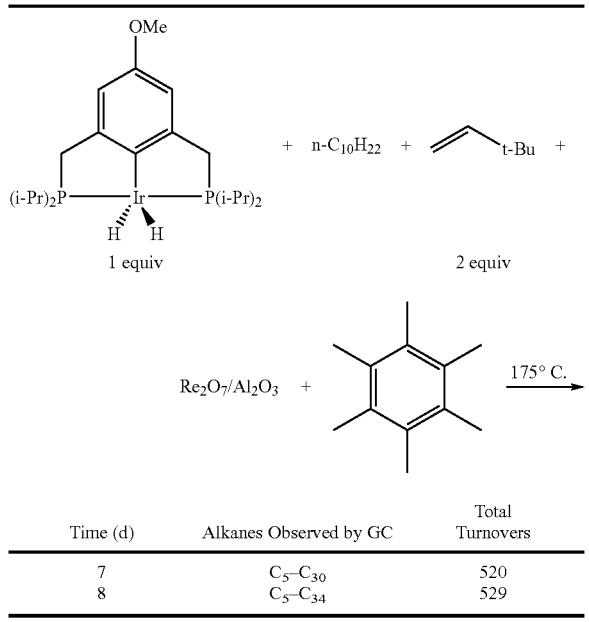

| Time (d) | Alkanes Observed by GC | Total Turnovers |
|---|---|---|
| 7 | $C_5$–$C_{30}$ | 520 |
| 8 | $C_5$–$C_{34}$ | 529 |

Total turnovers = $C_7 + C_8 + C_9 + C_{11} + C_{12} + C_{13} + [(C_{14} \times C_{15} \times C_{16} \times C_{17} \times C_{18}) \times 2] + C_{19}$ and up

Example 11

Procedures for Reactions with Heterogeneous Transfer Dehydrogenation and Olefin Metathesis Catalysts: $\{C_6H_3\text{-}2,6\text{-}[OP(t\text{-}Bu)_2]_2\}Ir(C_2H_4)/Al_2O_3$ and $Re_2O_7/Al_2O_3$ Alternatively, 221 mg of $\{C_6H_3\text{-}2,6\text{-}[OP(t\text{-}Bu)_2]_2\}Ir(C_2H_4)$ supported on alumina (6% Ir by weight) was weighed into a flask containing 288 mg of $Re_2O_7$ supported on alumina (12% Re by weight), 2.5 mL (12.8 mmol) of decane, and 11.4 mg (0.070 mmol) of hexamethylbenzene as internal standard. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers were calculated for each aliquot. Data is given in the Table below.

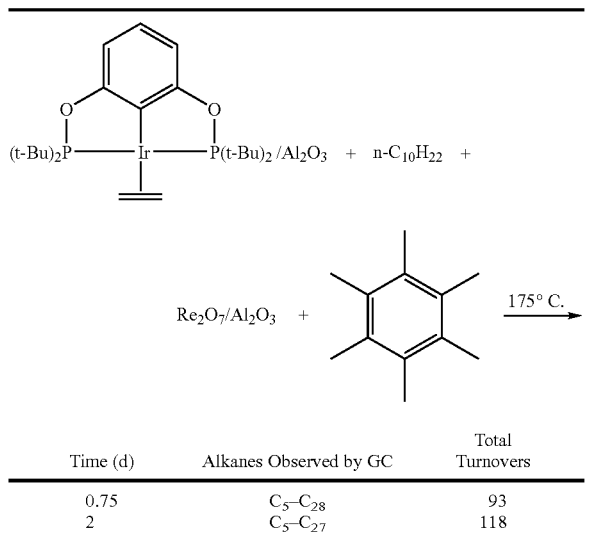

| Time (d) | Alkanes Observed by GC | Total Turnovers |
|---|---|---|
| 0.75 | $C_5$–$C_{28}$ | 93 |
| 2 | $C_5$–$C_{27}$ | 118 |

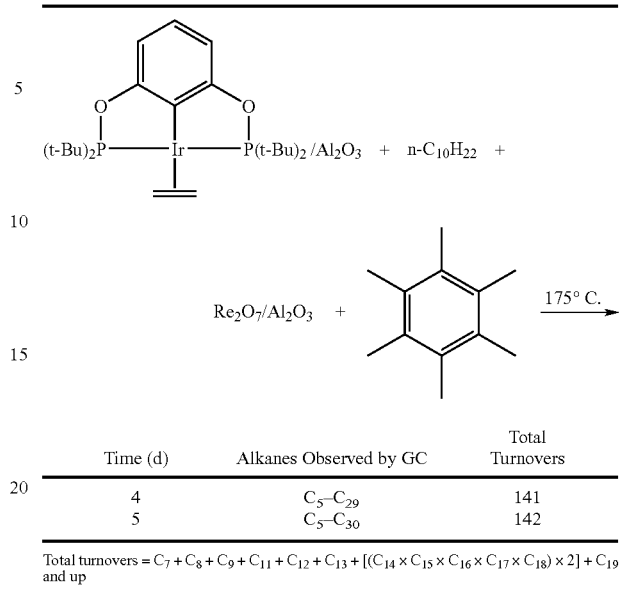

| Time (d) | Alkanes Observed by GC | Total Turnovers |
|---|---|---|
| 4 | $C_5$–$C_{29}$ | 141 |
| 5 | $C_5$–$C_{30}$ | 142 |

Total turnovers = $C_7 + C_8 + C_9 + C_{11} + C_{12} + C_{13} + [(C_{14} \times C_{15} \times C_{16} \times C_{17} \times C_{18}) \times 2] + C_{19}$ and up

Example 12

An example of alkane metathesis with $\{C_6H_3\text{-}2,6\text{-}[P(^tBu)_2]_2\}Ir(H_n)$ and $Mo(=CHCMe_2Ph)(=NC_6H_4(^iPr)_2)(OC(CF_3)_2(Me))_2$ All manipulations were carried out under argon atmosphere using standard Schlenk and glove box techniques. $\{C_6H_3\text{-}2,6\text{-}[P(^tBu)_2]_2\}Ir(H_n)$ was synthesized by a reported procedure. $Mo(=CHCMe_2Ph)(=NC_6H_4(^iPr)_2)(OC(CF_3)_2(Me))_2$ was purchased from Strem chemicals and used as supplied. Anhydrous n-hexane was purchased from Aldrich and stored under argon. tert-butyl ethylene was obtained from Aldrich and distilled over Na—K alloy, degassed via freeze pump thaw cycles and stored under argon.

Physical Measurements. $^1H$, $^{31}P\{^1H\}$, $^{19}F$ and $^{13}C\{^1H\}$-NMR (inverse gated with 5 sec delay) were recorded on a 400 MHz Varian NMR spectrometer using mesitylene-$d_{12}$ as an external lock. $^1H$ and $^{13}C\{^1H\}$-NMR were referenced to n-hexane that was in turn referenced to TMS. $^{31}P$-NMR was referenced to $PMe_3$ as an external standard. GC analyses were carried out using Thermo Focus GC instrument with a 25 m×0.2 mm×0.5 μm film thickness HP-1 cross-linked Methyl Silicone capillary column.

Experimental. $\{C_6H_3\text{-}2,6\text{-}[P(^tBu)_2]_2\}Ir(H_n)$ (12 mg, 0.0204 mmol), $Mo(=CHCMe_2Ph)(=NC_6H_4(^iPr)_2)(OC(CF_3)_2(Me))_2$ (25 mg, 0.0326 mmol) and tert-butyl ethylene (5.3 μl, 0.0408 mmol) were added to n-hexane (2 ml, 15.29 mmol) under argon atmosphere. 0.5 ml of the above solution was transferred to a 5 mm NMR tube containing $PMe_3$/Mesitylene-$d_{12}$ as an external lock. The contents were cooled under liquid nitrogen and the NMR tube sealed under vacuum. The tube was kept in a pre-heated oven at 110° C. and NMR spectra were recorded after regular intervals. When inverse gated $^{13}C\{^1H\}$-NMR experiment did not show further change, the NMR tube was cooled to room temperature and the seal was broken. Mesitylene (5 μl, 0.0359 mmol) was added to the NMR tube as an internal standard for GC. The sample was further analyzed by GC.

Figure 3A:
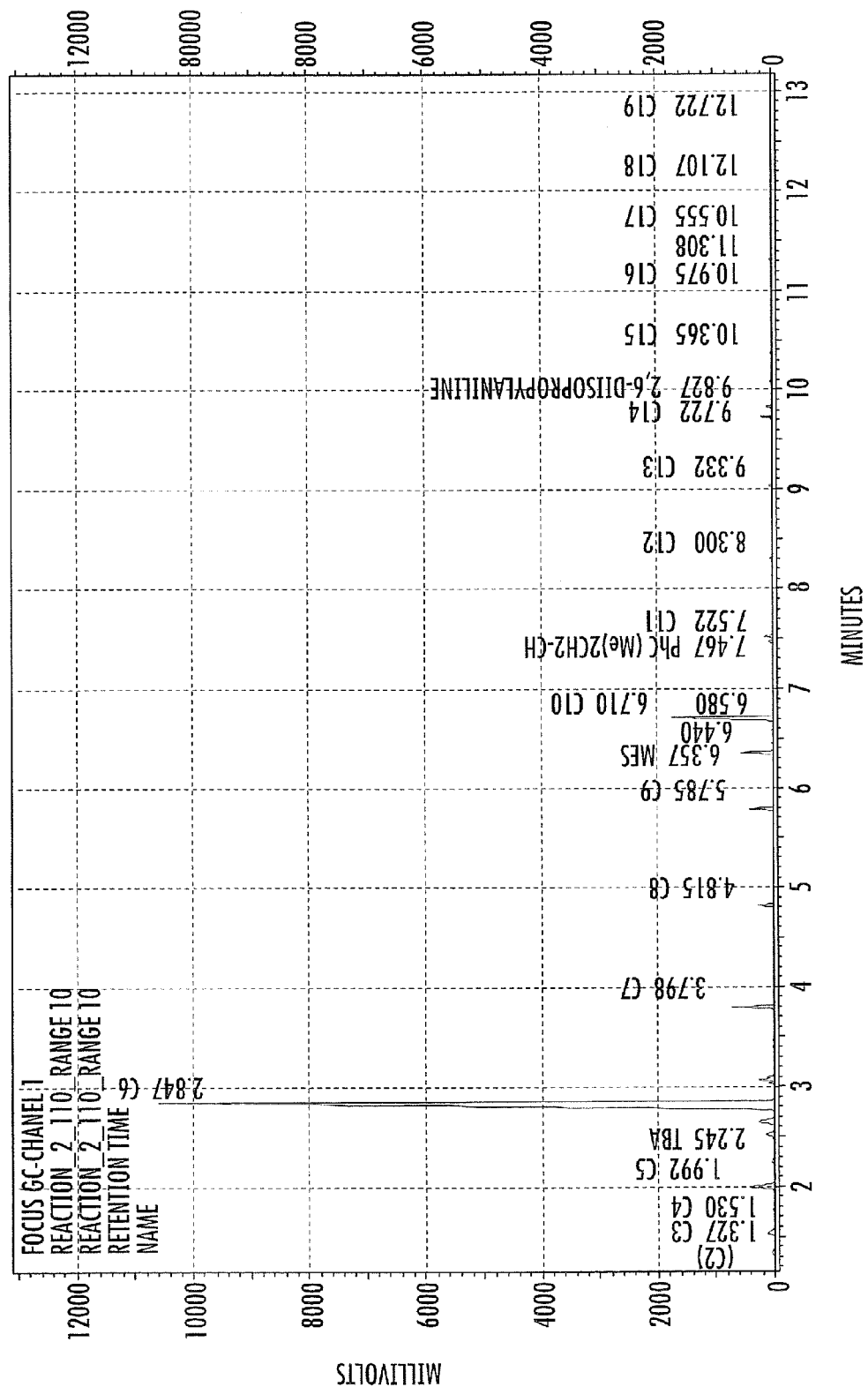
FIG. 3A is a gas chromatogram of the reaction product of the process of Example 12
Figure 3B:
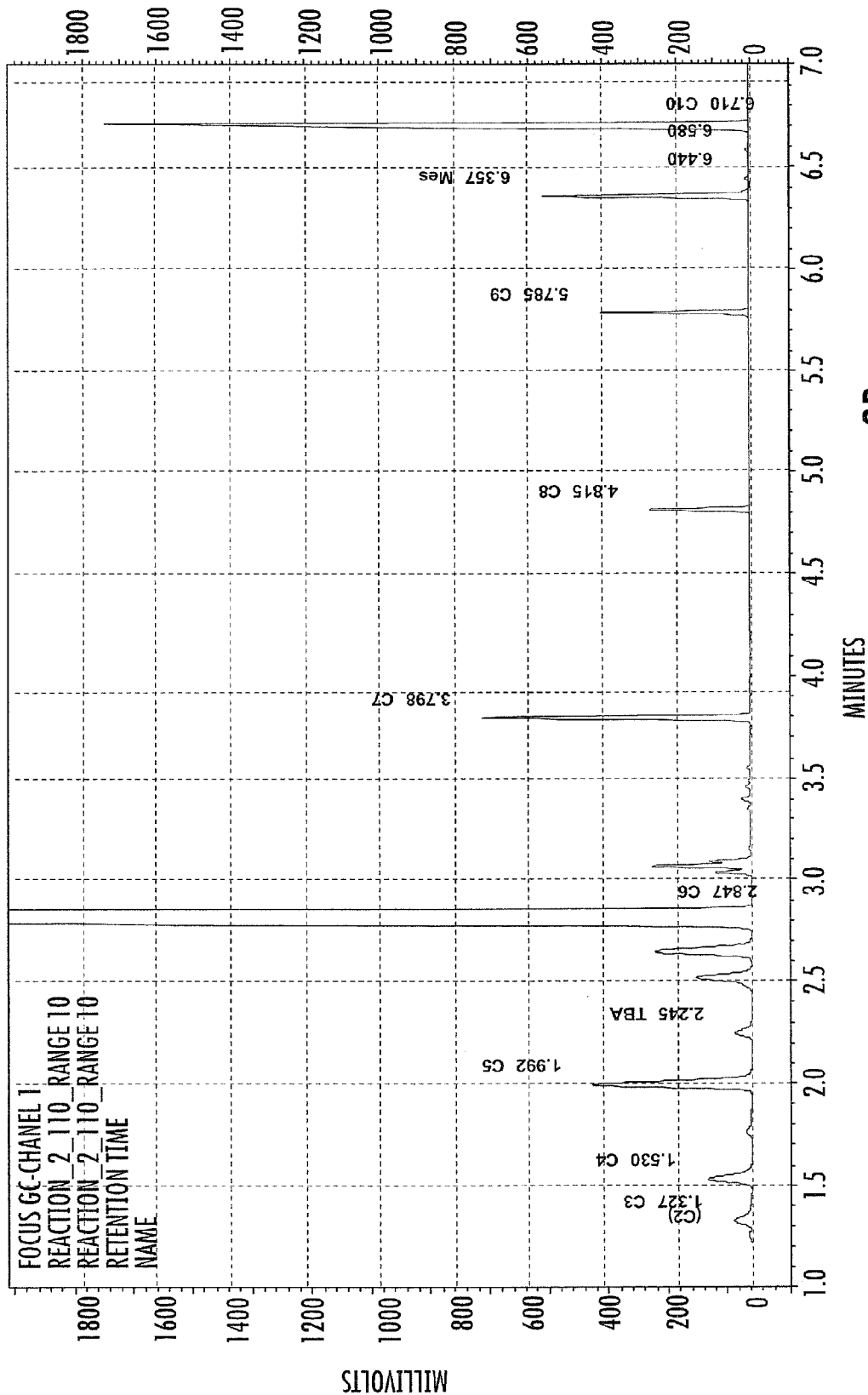
FIG. 3B is an expansion of an area of the chromatogram of FIG. 3A.
Figure 3C:
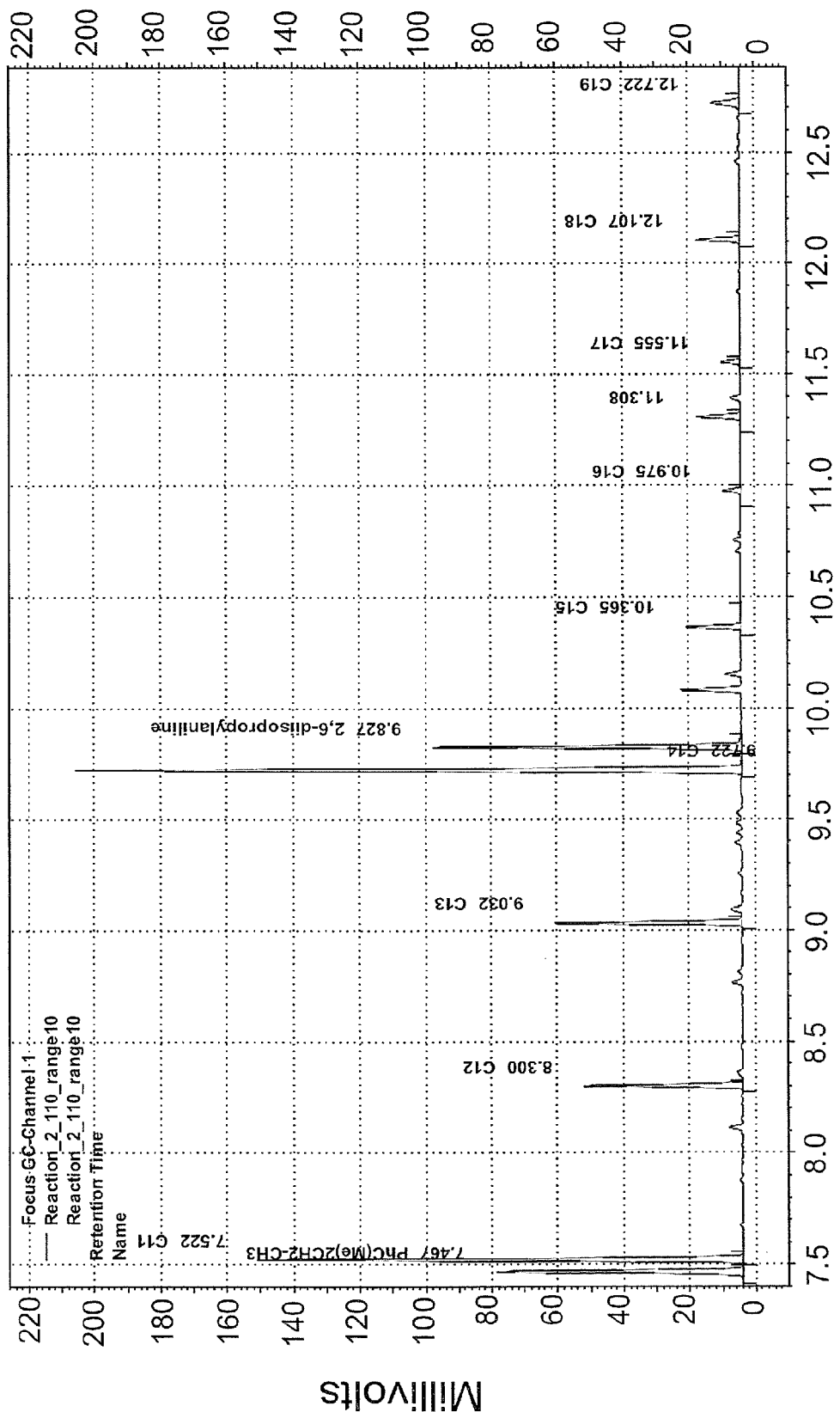
FIG. 3C is an expansion of an area of the chromatogram of FIG. 3A.

GC Results. The gas chromatogram shown in FIGS. 3A, 3B, and C3 (where 3B and 3C are expansions of areas of 3A) showed the distribution of various products formed during the reaction. The concentration of various alkanes were calculated with respect to the known concentration of mesitylene. The data has been shown in the excel sheet attached. The preliminary results show that about 15.5% of hexane has been consumed and 6.7% of n-decane is formed. About 2.6% of n-pentane and 2% n-heptane are formed along with the other alkanes in smaller quantities.

NMR Results. $^{13}C\{^1H\}$-NMR showed distinct peaks for the alkanes that could be assigned precisely. But this assignment was not exhaustive due to overlap of peaks for certain alkanes. Since decane was formed in a large amount and also showed clearly separated peaks in NMR, an inverse gated $^{13}C\{^1H\}$-NMR experiment with 5 sec delay was used to quantify the amount of decane formed during the reaction. It indicated the formation of about 7% of n-decane, which is very similar to the percentage that was obtained from GC.

Examples 13-17

Procedures for Alkane Metathesis Reactions Displaying an "Alumina Effect"

Example 13

Alkane Metathesis in the Absence of Additional Calcined, Free Al$_2$O$_3$

A flask was charged with 14.0 mg (0.227 mmol) of $\{C_6H_3\text{-}2,6\text{-}[OP(t\text{-}Bu)_2]_2\}Ir(C_2H_4)$, 540 mg of Re$_2$O$_7$/Al$_2$O$_3$ (3% by weight), 2.5 mL (12.8 mmol) of n-decane, and 12.5 mg (0.0770 mmol) of hexamethylbenzene as internal standard. The iridium complex immediately adsorbed itself onto the alumina support, as observed by the colorless solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers and product concentrations were calculated for each aliquot.

Example 14

Alkane Metathesis in the Presence of Additional Calcined, Free Al$_2$O$_3$

A flask was charged with 14.5 mg (0.0235 mmol) of $\{C_6H_3\text{-}2,6\text{-}[OP(t\text{-}Bu)_2]_2\}Ir(C_2H_4)$, 542 mg of Re$_2$O$_7$/Al$_2$O$_3$ (3% by weight), 500 mg of calcined, free γ-Al$_2$O$_3$, 2.5 mL (13 mmol) of n-decane, and 17.4 mg (0.107 mmol) of hexamethylbenzene as internal standard. The iridium complex immediately adsorbed itself onto the alumina support, as observed by the colorless solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers and product concentrations were calculated for each aliquot.

Data for Examples 13-14

| % loading | | Weight | Weight | [Product] (M) | | |
|---|---|---|---|---|---|---|
| Re$_2$O$_7$ | Ir: Re$_2$O$_7$ | Re$_2$O$_7$/Al$_2$O$_3$ | Added Al$_2$O$_3$ | 3 hrs | 5 days | End of rxn |
| 3 | 1:1.5 | 540 mg | 0 mg | .153 | 1.3 | 1.6 (12 d) |
| 3 | 1:1.5 | 542 mg | 500 mg | .281 | 2.0 | 2.9 (8 d) |

Example 15

Alkane Metathesis in the Absence of Additional Calcined, Free Al$_2$O$_3$

A flask was charged with 13.0 mg (0.0210 mmol) of $\{C_6H_3\text{-}2,6\text{-}[OP(t\text{-}Bu)_2]_2\}Ir(C_2H_4)$, 128 mg of Re$_2$O$_7$/Al$_2$O$_3$ (13% by weight), 2.5 mL (12.8 mmol) of n-decane, and 13.4 mg (0.0826 mmol) of hexamethylbenzene as internal standard. The iridium complex partially adsorbed itself onto the alumina support, as observed by the light orange solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers and product concentrations were calculated for each aliquot.

Example 16

Alkane Metathesis in the Presence of Additional Calcined, Free Al$_2$O$_3$

A flask was charged with 13.5 mg (0.0219 mmol) of $\{C_6H_3\text{-}2,6\text{-}[OP(t\text{-}Bu)_2]_2\}Ir(C_2H_4)$, 130 mg of Re$_2$O$_7$/Al$_2$O$_3$ (13% by weight), 415 mg of calcined, free ≠-Al$_2$O$_3$, 2.5 mL (12.8 mmol) of n-decane, and 11.7 mg (0.0721 mmol) of hexamethylbenzene as internal standard. The iridium complex immediately adsorbed itself onto the alumina support, as observed by the colorless solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers and product concentrations were calculated for each aliquot.

Data for Examples 15-16

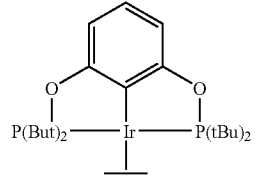

| % loading | | Weight | Weight | [Product] (M) | | |
|---|---|---|---|---|---|---|
| Re$_2$O$_7$ | Ir: Re$_2$O$_7$ | Re$_2$O$_7$/Al$_2$O$_3$ | Added Al$_2$O$_3$ | 3 hrs | 5 days | End of rxn |
| 13 | 1:1.5 | 128 mg | 0 mg | trace | — | .040 (2 d) |
| 13 | 1:1.5 | 130 mg | 415 mg | .196 | 1.3 | 1.7 (9 d) |

Example 17

Alkane Metathesis in the Absence of Additional Calcined, Free Al$_2$O$_3$

A flask was charged with 53.7 mg of MoO$_3$/SiO$_2$-Al$_2$O$_3$ (9.1% by weight), 0.90 μL (0.0065 mmol) of SnMe$_4$, 2.5 mL (13 mmol) of n-decane, and 6.0 μL (0.067 mmol) of benzene as internal standard. The mixture was stirred at room temperature for 10 min, followed by the addition of 14.1 mg (0.0228 mmol) of $\{C_6H_3$-2,6-[OP(t-Bu)$_2$]$_2\}$Ir(C$_2$H$_4$) to the mixture. The iridium complex partially adsorbed itself onto the alumina support, as observed by the light orange solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers and product concentrations were calculated for each aliquot.

Example 18

Alkane Metathesis in the Presence of Additional Calcined, Free Al$_2$O$_3$

A flask was charged with 53.9 mg of MoO$_3$/SiO$_2$—Al$_2$O$_3$ (9.1% by weight), 0.90 μL (0.0065 mmol) of SnMe$_4$, 2.5 mL of n-decane, and 6.0 μL (0.067 mmol) of benzene as internal standard. The mixture was stirred at room temperature for 10 min, followed by addition of 12.6 mg (0.0204 mmol) of $\{C_6H_3$-2,6-[OP(t-Bu)$_2$]$_2\}$Ir(C$_2$H$_4$) and 300 mg of calcined, free γ-Al$_2$O$_3$. The iridium complex immediately adsorbed itself onto the alumina support, as observed by the colorless solution and rust-colored solid. The flask was sealed tightly with a teflon plug under an argon atmosphere, and the solution stirred in a 175° C. oil bath. Periodically, the flask was removed from the bath and cooled. An aliquot was removed from the flask, and analyzed by GC. Turnover numbers and product concentrations were calculated for each aliquot.

Data for Examples 17-18

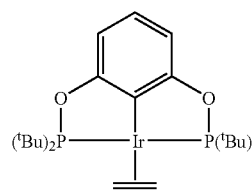

| % weight | | Weight | Weight | [Product] (M) | | |
|---|---|---|---|---|---|---|
| MoO$_3$ | Ir: MoO$_3$ | MoO$_3$/SiO$_2$—Al$_2$O$_3$ | Added Al$_2$O$_3$ | 3 hrs | 5 days | End of rxn |
| 9.1 | 1:1.6 | 54 mg | 0 mg | .007 | .022 | .026 (7 d) |
| 9.1 | 1:1.6 | 54 mg | 300 mg | .071 | 1.0 | 1.7 (30 d) |

In the reactions above, we observe a significant increase in reaction rate and in product concentration upon addition of calcined, free $Al_2O_3$. It is known that $\{C_6H_3\text{-}2,6\text{-}[OP(t\text{-}Bu)_2]_2\}Ir(C_2H_4)$ supports itself to the solid support in these reactions, as observed by the change from a red solution and white solid to a colorless (or lightly colored) solution and rust-colored solid. Thus, we attribute this effect of added alumina on reaction rate and yield to an equilibrium between the supported and free Ir catalyst, which favors the supported complex in the presence of the added $Al_2O_3$. The free Ir complex may interact with the $Re_2O_7$ or $MoO_3$ complex on the solid support and deactivate the metathesis catalyst. Thus, in the presence of added alumina, an increase in the amount of supported $\{C_6H_3\text{-}2,6\text{-}[OP(t\text{-}Bu)_2]_2\}Ir(C_2H_4)$, relative to free Ir, may decrease interaction between the two catalysts and decrease the amount of catalyst deactivation.

Examples 19-20

Synthesis of $SiO_2$-Supported Ir $H_2$ Transfer Catalyst

Example 19

Sequence for Preparing $SiO_2$-Supported Ir $H_2$ Transfer Catalyst

The Pd-catalyzed cross-coupling reaction of 5-Bromo-1,3-dimethoxybenzene with allyl boronic acid pinacol ester produced 5-allyl-1,3-dimethoxybenzene 1 in excellent yield. $AlI_3$ will be used for demethylating 5-Allyl-1,3-dimethoxybenzene with $CS_2$ as solvent to produce 5-allylresorcinol 2. The bis(phosphinite) PCP ligands 3 will be obtained by diphosphorylation of 5-allylresorcinol 2 with the respective chlorophosphine and sodium hydride as a base. Iridium complexes 4 will be obtained from reaction of the respective PCP ligands 3 with $[Ir(COD)Cl]_2$ or $[Ir(COE)_2Cl]_2$. Hydrosilylation of complexes 4 will produce the hydrosilylated complexes 5. Reaction of complexes 5 with silica gel will afford the $Si_2O$-supported Ir complexes 6. To date, 5-allyl-1,3-dimethoxybenzene 1 has been prepared in 92% yield.

Scheme for preparing $SiO_2$-supported Ir $H_2$ transfer catalyst

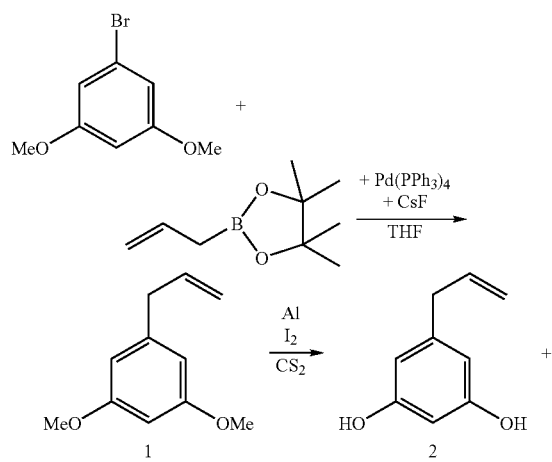

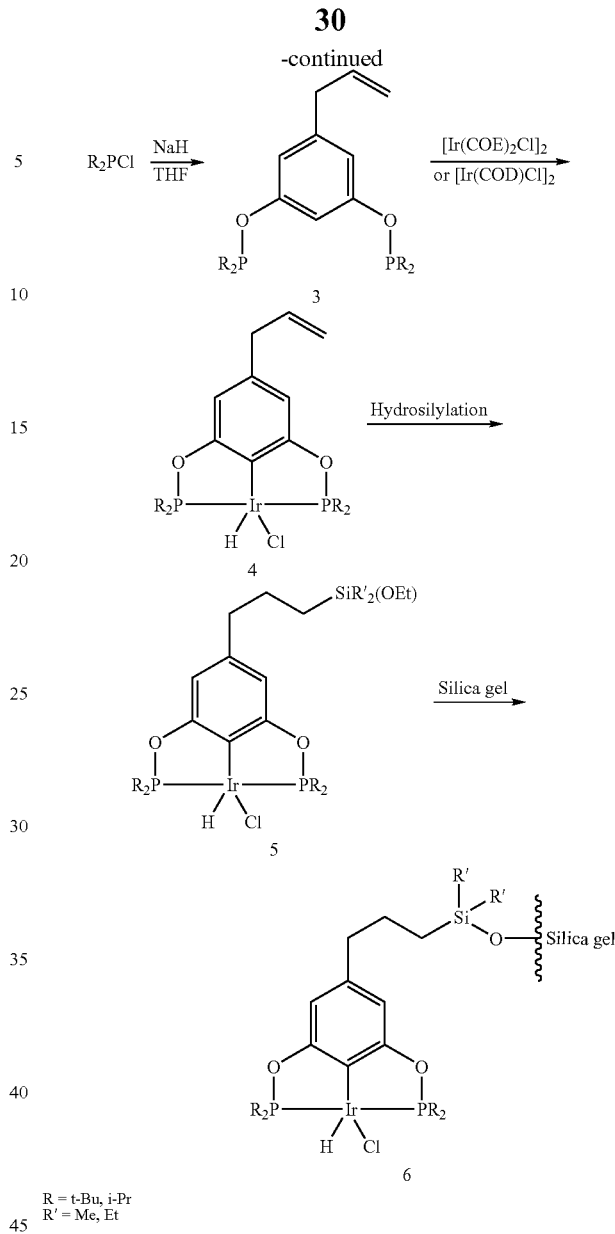

Example 20

Synthesis of 5-Allyl-1,3-dimethoxybenzene

5-Bromo-1,3-dimethoxybenzene (2.13 g, 9.8 mmol), CsF (2.88 g, 19.0 mmol), and $Pd(Ph_3)_4$ (0.57-1.13 g, 0.5-1.0 mmol) were weighed into a flame-dried Schlenk flask and put under a flow of argon. THF (80 mL) was added to the flask via syringe, and the resulting suspension was stirred for 30 min at room temperature. Allyl boronic acid pinacol ester (2.96 g, 17.6 mmol) in THF (40 ml) was added and the resulting mixture was heated to reflux for 30 h. Another portion of CsF (2.88 g, 19.0 mmol) and $Pd(Ph_3)_4$ (0.57-1.13 g, 0.5-1.0 mmol) were added and the reaction was continued to reflux for 24 h. The reaction mixture was diluted with petroleum ether (100 ml) followed by $H_2O$ (100 ml). The layers were separated and the aqueous layer was extracted with petroleum ether (2×80 ml). The combined organic layers were washed with $H_2O$ (100 ml), and brine (100 ml). The solution was dried over MgSO$_4$ and evaporated to dryness. The crude product was purified by column chromatography (silica, eluent: hexanes/benzene=3:2) to give 1.60 g (92%) of 5-Allyl-1,3-dimethoxybenzene. $^1$H NMR (CDCl$_3$): δ 3.33 (d, J=6.7 Hz, 2H, CH$_2$CH=CH$_2$), 3.77 (s, 6H, OCH$_3$), 5.02-5.11 (m, 2H, CH$_2$CH=CH$_2$), 5.89-5.99 (m, 1H, CH$_2$CH=CH$_2$), 6.33-6.38 (m, 3H).

Example 21

An Example of Alkane Metathesis with {C$_6$H$_3$-2,6-[P($^t$Bu)$_2$]$_2$}Ir(H$_n$) and Mo(=CHCMe$_2$Ph)(=NC$_6$H$_4$($^i$Pr)$_2$)(OC(CF$_3$)$_2$(Me))$_2$ General Remarks. All manipulations were carried out under argon atmosphere using standard Schlenk and glove box techniques. {C$_6$H$_3$-2,6-[P($^t$Bu)$_2$]$_2$}Ir(H$_n$) was synthesized by a reported procedure. Mo(=CHCMe$_2$Ph)(=NC$_6$H$_4$($^i$Pr)$_2$)(OC(CF$_3$)$_2$(Me))$_2$ was purchased from Strem chemicals and used as supplied. Anhydrous n-hexane (99%) was purchased from Fluka, degassed via freeze pump thaw cycles, distilled over NaK and stored under argon in the glove box. tert-butyl ethylene was obtained from Aldrich. It was degassed via freeze pump thaw cycles, stirred over Na—K alloy, collected by vacuum transfer and then stored under argon.

Physical Measurements. $^1$H, $^{31}$P{$^1$H} and $^{13}$C{$^1$H}-NMR (inverse gated with 5 sec delay) were recorded on a 400 MHz Varian NMR spectrometer using mesitylene-d$_{12}$ as an external lock. $^1$H and $^{13}$C{$^1$H}-NMR were referenced to n-hexane that was in turn referenced to TMS. $^{31}$P-NMR was referenced to PMe$_3$ as an external standard (δ=−62.6 ppm). GC analyses were carried out using Thermo Focus GC instrument with a 25 m×0.2 mm ID×0.5 μm film thickness HP-1 cross-linked Methyl Silicone capillary column (used primarily for the analysis of alkanes C$_n$≧4). The headspace analysis was carried out on Thermo Focus GC instrument fitted with a 100 m×0.25 mm ID×0.5 μm film thickness Supelco Petrocol DH capillary column (used primarily for the analysis of alkanes C$_n$≦4).

Figure 4:
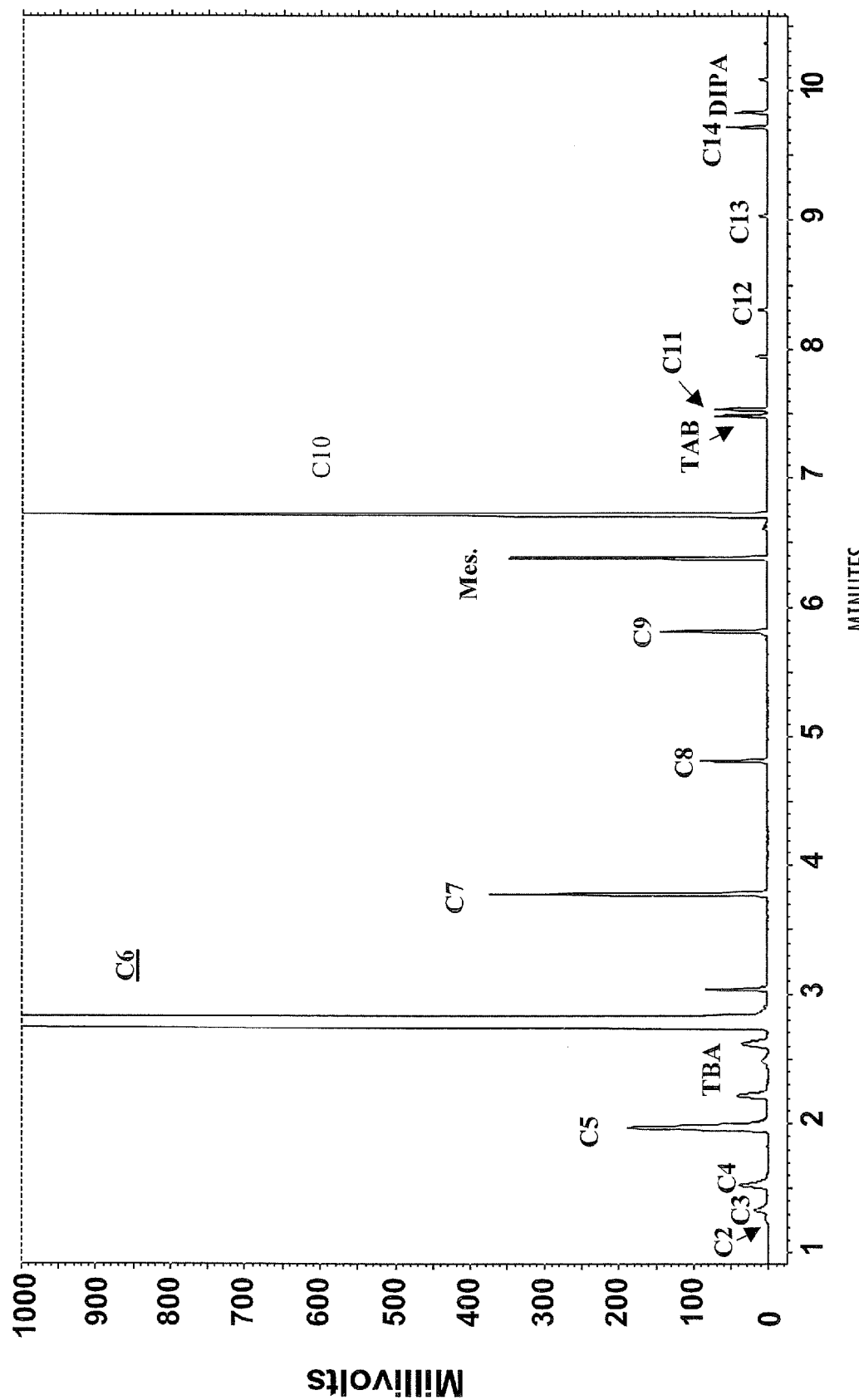
FIG. 4: Gas chromatogram showing product distribution from tandem reaction of ($^{tBu}$PCP)IrHn with Mo-Schrock in n-hexane at 125° C. in a sealed tube for 23 h. TBA=2,2-dimethylbutane (from hydrogenation of 3,3-dimethyl-1-butene) Mes.=Mesitylene (Internal standard), TAB=tert-amyl benzene (from hydrogenation of 3-methyl-3-phenyl-1-butene (loss of 2-methyl-2-phenylpropylidene ligand on Mo), DIPA=2,6-diisopropylaniline.

Experimental. In the glovebox, ($^t$BuPCP)IrH$_n$ (12 mg, 0.021 mmol), Mo-Schrock (10 mg, 0.013 mmol) and TBE (5.4 μl, 0.042 mmol) were added to n-hexane (2 mL, 15.3 mmol) containing mesitylene (0.034 M as an internal standard). Two aliquots of this solution (0.5 mL each) were transferred to NMR tubes containing capillaries of PMe$_3$ in mesitylene-d$_{12}$ for reference and locking. The contents were cooled under liquid nitrogen and sealed under vacuum. The tubes were heated (in parallel) in a preheated oven at 125° C. and NMR spectra were recorded at regular intervals. $^{13}$C{$^1$H}-NMR spectroscopy permits the resolution of all n-alkanes in the range C1-C12 although quantification is significantly less precise than is obtained by GC analysis (but improved by the use of inverse gating). No significant differences between spectra of the two aliquots were observed. When NMR did not show any further change in the composition of n-alkanes (23 h), the reaction mixture was analyzed by GC. The seal of one of the tubes was broken, and the solution and headspace were analyzed by GC. The seal of the second tube was broken inside the glove box, another lot of catalyst Mo-Schrock (2.5 mg, 0.003 mmol) was added, and the tube was sealed again under vacuum and heated in the oven at 125° C. for another 23 h. The solution and headspace were then analyzed in the same manner. The results obtained from GC are shown in the Table below and the GC trace is given in FIG. 4.

TABLE

Product distribution from tandem reaction of ($^{tBu}$PCP) IrHn (10 mM) with Mo-Schrock (6.5 mM) and tert-butylethylene (TBE; 20 mM) in n-hexane (2 ml) at 125° C. in a sealed tube for 23 h.

| Entry | Time (h) | C$_2$ (mM) | C$_3$ (mM) | C$_4$ (mM) | C$_5$ (mM) | C$_7$ (mM) | C$_8$ (mM) | C$_9$ (mM) | C$_{10}$ (mM) | C$_{11}$ (mM) | C$_{12}$ (mM) | C$_{13}$ (mM) | C$_{14}$ (mM) | C$_{≧15}$ (mM) | Total Product (M) |
|---|---|---|---|---|---|---|---|---|---|---|---|---|---|---|---|
| 1 | 23 | 131 | 176 | 127 | 306 | 155 | 37 | 49 | 232 | 18 | 4 | 4 | 10 | 2 | 1.25 |
| 2* | 46 | 189 | 255 | 193 | 399 | 208 | 61 | 81 | 343 | 31 | 9 | 9 | 22 | 7 | 1.81 |

*After additional 6.5 mM Mo-Schrock catalyst.

Analysis of Headspace. (Authentic samples of methane, ethane, and propane were used for calibration). After heating, the contents of the tube were brought to RT and the tube was then cooled under liquid nitrogen and shaken repeatedly to equilibrate and dissolve the gaseous products. The seal was then broken and replaced with a septum and the solution was brought to RT. 200 μl of the headspace was sampled using a gas tight syringe and analyzed by GC. The GC analysis of the gas phase indicated the presence of 1.7 μmol of ethane accounting for 131 mM of total ethane if all the ethane were in solution. Likewise, a small amount of propane in the headspace accounted for 1 mM of propane adding to a total concentration of 176 mM of propane. Only trace quantities of methane were observed (effective concentration=0.5 mM), probably formed due to decomposition of Mo-methylidene intermediate.

Different product distributions have been observed on comparing the reactions carried out with $(^{tBu}PCP)IrH_n$ and $(^{tBu}POCOP)IrH_n/(^{tBu}POCOP)Ir(C_2H_4)$ using Mo-Schrock as metathesis catalyst. Reaction with $(^{tBu}POCOP)IrH_n$ as dehydrogenation catalyst resulted in a stochastic distribution of products, whereas reaction with $(^{tBu}PCP)IrH_n$ gave higher concentration of $C_{2n-2}$ product starting from $C_n$. Presumably, under the conditions of this reaction, diphosphine-ligated Ir catalyst catalyzes isomerization more slowly (or more slowly relative to hydrogenation) than does the diphosphinite-ligated Ir species.

The foregoing is illustrative of the present invention, and is not to be construed as limiting thereof. The invention is defined by the following claims, with equivalents of the claims to be included therein.

That which is claimed is:

1. A method of converting at least one first alkane to a mixture of at least one lower molecular weight alkane and at least one higher molecular weight alkane, comprising:
   reacting a first alkane in the presence of a dual catalyst system comprising: (i) a hydrogen transfer catalyst and (ii) a metathesis catalyst to produce said mixture of at least one low molecular weight alkane and at least one high molecular weight alkane, said reacting step carried out at a temperature not greater than 300° C. and in the presence of a hydrogen acceptor, and wherein the molar ratio of said hydrogen acceptor to said hydrogen transfer catalyst is not greater than 10:1;
   wherein said hydrogen transfer catalyst is an iridium pincer complex catalyst;
   and wherein said metathesis catalyst is selected from the group consisting of Schrock catalysts, molybdenum catalysts, tungsten oxide catalysts, rhenium oxide catalysts, and mixtures thereof.

2. The method of claim 1, wherein both said hydrogen transfer catalyst and said metathesis catalyst are heterogeneous catalysts.

3. The method of claim 1, wherein said metathesis catalyst is selected from the group consisting of Schrock catalysts.

4. The method of claim 1, wherein said at least one higher molecular weight alkane is produced at a ratio of linear alkanes to branched alkanes of at least 500:1.

5. The method of claim 1, wherein said hydrogen transfer catalyst is immobilized on a solid support, wherein said reaction is carried out in a solvent, and wherein said method further comprises the step of separating free hydrogen transfer catalyst from said solvent.

6. The method of claim 1, wherein said at least one first alkane is linear.

7. The method of claim 1, wherein said at least one first alkane is produced by:
   converting synthesis gas to said at least one first alkane by Fischer-Tropsch catalysis.

8. The method of claim 1, further comprising the step of:
   providing at least a portion of said high molecular weight alkane to a liquid hydrocarbon fuel synthesis process to produce liquid hydrocarbon fuel.

9. The method of claim 1, further comprising the step of:
   providing at least a portion of said high molecular weight alkane to a gasoline synthesis process to produce gasoline.

10. The method of claim 1, further comprising the step of:
    providing at least a portion of said high molecular weight alkane to a diesel fuel synthesis process to produce diesel fuel.

11. In a method of making a liquid hydrocarbon fuel from a synthesis gas by the Fischer Tropsch reaction, wherein said fuel comprises at least one high molecular weigh alkane, and wherein at least a portion of the product of said Fischer Tropsch reaction comprises at least one low molecular weight alkane, the improvement comprising:
    converting at least a portion of said low molecular weight alkane to said high molecular weight alkane by reacting said low molecular weight alkane in the presence of a dual catalyst system comprising: (i) a hydrogen transfer catalyst and (ii) a metathesis catalyst to produce said high molecular weight alkane said reacting carried out at a temperature not greater than 300° C. and in the presence of a hydrogen acceptor, and wherein the molar ratio of said hydrogen acceptor to said hydrogen transfer catalyst is not greater than 10:1;
    wherein said hydrogen transfer catalyst is an iridium pincer complex catalyst;
    and wherein said metathesis catalyst is selected from the group consisting of Schrock catalysts, molybdenum catalysts, tungsten oxide catalysts, rhenium oxide catalysts, and mixtures thereof.

12. The method of claim 11, wherein said both said hydrogen transfer catalyst and said metathesis catalyst are heterogeneous catalysts.

13. The method of claim 11, wherein said metathesis catalyst is selected from the group consisting of Schrock catalysts.

14. The method of claim 11, wherein said at least one higher molecular weight alkane is produced at a ratio of linear alkanes to branched alkanes of at least 500:1.

15. The method of claim 11, wherein said hydrogen transfer catalyst is immobilized on a solid support, wherein said reaction is carried out in a solvent, and wherein said method further comprises the step of separating free hydrogen transfer catalyst from said solvent.

16. The method of claim 11, wherein said fuel is diesel fuel or gasoline.

17. The method of claim 11, wherein:
    said at least one low molecular weight alkane is a compound of the formula $C_nH_{2n+2}$ where n is 3-10, and
    said at least one high molecular weight alkane is a compound of the formula $C_mH_{2m+2}$, where m is an integer of from 4 to 40.

18. In a method of making a liquid hydrocarbon fuel from a synthesis gas by the Fischer-Tropsch reaction, wherein said fuel comprises at least one high molecular weigh alkane, wherein at least a portion of the product of said Fischer Tropsch reaction comprises a wax, and wherein said wax is of still higher molecular weight than said high molecular weight alkane, the improvement comprising:
    converting at least a portion of said wax to said at least one high molecular weight alkane by reacting said wax in the presence of a dual catalyst system comprising: (i) a hydrogen transfer catalyst and (ii) a metathesis catalyst to produce said at least one higher molecular weight alkane; said reacting carried out at a temperature not greater than 300° C. and in the presence of a hydrogen acceptor, and wherein the molar ratio of said hydrogen acceptor to said hydrogen transfer catalyst is not greater than 10:1;

wherein said hydrogen transfer catalyst is an iridium pincer complex catalyst;

and wherein said metathesis catalyst is selected from the group consisting of Schrock catalysts, molybdenum catalysts, tungsten oxide catalysts, rhenium oxide catalysts, and mixtures thereof.

19. The method of claim 18, wherein said both said hydrogen transfer catalyst and said metathesis catalyst are heterogeneous catalysts.

20. The method of claim 18, wherein said metathesis catalyst is selected from the group consisting of Schrock catalysts.

21. The method of claim 18, wherein said at least one higher molecular weight alkane is produced at a ratio of linear alkanes to branched alkanes of at least 500:1.

22. The method of claim 18, wherein said fuel is diesel fuel or gasoline.

23. The method of claim 18, wherein:
said at least one higher molecular weight alkane is a compound of the formula $C_mH_{2m+2}$, where m is an integer of from 4 to 40;
said wax comprises a compound of the formula $C_pH_{2p+2}$ where p is 18 to 200.

24. The method of claim 1, wherein said reacting step is carried out at atmospheric pressure at a temperature not greater than 200° C.

25. The method of claim 1, wherein said hydrogen transfer catalyst is a homogeneous catalyst;
wherein said alkane is provided as a mixed composition comprising both alkanes and alkenes, with the weight ratio of alkanes to alkenes being at least 50:1;
and wherein the at least one higher molecular weigh alkane produced by the reaction comprises a mixture of linear alkanes to branched alkanes at a molar ratio of at least 1000:1.

26. The method of claim 11, wherein said reacting step is carried out at atmospheric pressure at a temperature not greater than 200° C.

27. The method of claim 11, wherein said hydrogen transfer catalyst is a homogeneous catalyst;
wherein said alkane is provided as a mixed composition comprising both alkanes and alkenes, with the weight ratio of alkanes to alkenes being at least 50:1;
and wherein the at least one higher molecular weigh alkane produced by the reaction comprises a mixture of linear alkanes to branched alkanes at a molar ratio of at least 1000:1.

28. The method of claim 18, wherein said reacting step is carried out at atmospheric pressure at a temperature not greater than 200° C.

29. The method of claim 18, wherein said hydrogen transfer catalyst is a homogeneous catalyst;
wherein said alkane is provided as a mixed composition comprising both alkanes and alkenes, with the weight ratio of alkanes to alkenes being at least 50:1;
and wherein the at least one higher molecular weigh alkane produced by the reaction comprises a mixture of linear alkanes to branched alkanes at a molar ratio of at least 1000:1.

* * * * *

UNITED STATES PATENT AND TRADEMARK OFFICE
CERTIFICATE OF CORRECTION

PATENT NO.       : 7,902,417 B2
APPLICATION NO.  : 11/482324
DATED            : March 8, 2011
INVENTOR(S)      : Goldman et al.

It is certified that error appears in the above-identified patent and that said Letters Patent is hereby corrected as shown below:

In the Patent:

Column 5, Line 21: Please correct "A12O₃" to read -- $Al_2O_3$ --
         Line 25: Please correct "A12O₃" to read -- $Al_2O_3$ --

Column 6, Line 14: Please correct "W03" to read -- $WO_3$ --

Column 18, Example 6a, Lines 55-62: Please delete duplicate compound

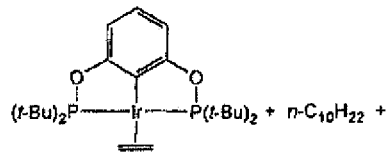

Column 19, Example 6a, Lines 19-26: Please delete duplicate compound

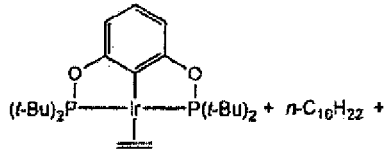

Column 20, Example 7, Line 50: Please correct "+ C.and" to read -- + $C_{19}$ and --

Column 26, Line 57: Please correct "free ≠" to read -- free γ --

Signed and Sealed this
Fifteenth Day of November, 2011

David J. Kappos
*Director of the United States Patent and Trademark Office*